(12) United States Patent
Clark et al.

(10) Patent No.: US 12,383,129 B2
(45) Date of Patent: Aug. 12, 2025

(54) MEDICAL DEVICES WITH BATTERY REMOVAL

(71) Applicant: COOPERSURGICAL, INC., Trumbull, CT (US)

(72) Inventors: Adrienne Clark, Waltham, MA (US); Demetrio Donald Anaya, Somerville, MA (US); Shawn P. Murphy, Bolton, MA (US)

(73) Assignee: CooperSurgical, Inc., Trumbull, CT (US)

( * ) Notice: Subject to any disclaimer, the term of this patent is extended or adjusted under 35 U.S.C. 154(b) by 1030 days.

(21) Appl. No.: 17/212,506

(22) Filed: Mar. 25, 2021

(65) Prior Publication Data

US 2021/0204805 A1 Jul. 8, 2021

Related U.S. Application Data

(63) Continuation of application No. 16/402,580, filed on May 3, 2019, now Pat. No. 11,253,145, which is a
(Continued)

(51) Int. Cl.
*A61B 1/32* (2006.01)
*A61B 1/00* (2006.01)
(Continued)

(52) U.S. Cl.
CPC ............ *A61B 1/32* (2013.01); *A61B 1/00032* (2013.01); *A61B 1/00066* (2013.01);
(Continued)

(58) Field of Classification Search
CPC ... A61B 1/32; A61B 1/00032; A61B 1/00066; A61B 1/00108; A61B 1/0684; A61B 1/267; A61B 1/303; A61B 1/31
See application file for complete search history.

(56) References Cited

U.S. PATENT DOCUMENTS

| 559,122 A | 4/1896 | Daily |
| 659,182 A | 10/1900 | Pilling |

(Continued)

FOREIGN PATENT DOCUMENTS

| CN | 2239235 Y | 11/1996 |
| CN | 2265156 Y | 10/1997 |

(Continued)

OTHER PUBLICATIONS

International Search Report for International application No. PCT/US2021/017768 issued May 27, 2021, a copy of which is enclosed.
(Continued)

*Primary Examiner* — Lynnsy M Summitt
(74) *Attorney, Agent, or Firm* — Fish & Richardson P.C.

(57) ABSTRACT

A battery-powered medical device comprising: an outer housing having an opening formed therein; at least one power source housed within the outer housing, the outer housing being configured to at least partially enclose the at least one power source so as to prevent contamination of the at least one power source with biohazardous materials, and the at least one power source being removable from the outer housing via the opening; a cover configured to cover the opening in the outer housing and to retain the at least one power source within the outer housing, and an actuator provided within the outer housing that directly engages with a portion of the at least one power source when the cover covers the opening in the outer housing. The cover is configured to be operated to expose the opening in the outer housing, and when the cover is operated to expose the opening, the actuator is configured to pull the at least one power source from the outer housing and the outer housing is configured to release the at least one power source via the opening without requiring physical contact between the user and the at least one power source. The outer housing
(Continued)

comprises a handle and an operative portion coupled to the handle.

8 Claims, 24 Drawing Sheets

Related U.S. Application Data continuation of application No. 16/105,153, filed on Aug. 20, 2018, now Pat. No. 10,278,572.

(60) Provisional application No. 62/649,190, filed on Mar. 28, 2018, provisional application No. 62/574,969, filed on Oct. 20, 2017, provisional application No. 62/574,412, filed on Oct. 19, 2017.

(51) Int. Cl.
| | |
|---|---|
| *A61B 1/06* | (2006.01) |
| *A61B 1/267* | (2006.01) |
| *A61B 1/303* | (2006.01) |
| *A61B 1/31* | (2006.01) |
| *A61B 17/02* | (2006.01) |
| *A61B 17/00* | (2006.01) |

(52) U.S. Cl.
CPC ........ *A61B 1/00108* (2013.01); *A61B 1/0684* (2013.01); *A61B 1/267* (2013.01); *A61B 1/303* (2013.01); *A61B 1/31* (2013.01); *A61B 17/02* (2013.01); *A61B 2017/00734* (2013.01)

(56) References Cited

U.S. PATENT DOCUMENTS

| | | | |
|---|---|---|---|
| 2,235,979 A | 3/1941 | Brown | |
| 2,247,458 A | 7/1941 | Wintemberg | |
| 2,482,971 A | 9/1949 | Golson | |
| 2,592,190 A | 4/1952 | Rubens et al. | |
| 3,023,306 A | 2/1962 | Kester | |
| 3,324,850 A | 6/1967 | Gunning et al. | |
| 3,332,414 A | 7/1967 | Gasper | |
| 3,426,749 A | 2/1969 | Jephcott | |
| 3,532,088 A * | 10/1970 | Fiore | A61B 1/32 600/222 |
| 3,592,199 A | 7/1971 | Ostensen | |
| 3,595,222 A | 7/1971 | Vellacott | |
| 3,598,113 A | 8/1971 | Moore et al. | |
| 3,638,644 A | 2/1972 | Reick | |
| 3,650,266 A | 3/1972 | Pestka et al. | |
| 3,675,641 A | 7/1972 | Fiore | |
| 3,716,047 A | 2/1973 | Moore et al. | |
| 3,729,006 A | 4/1973 | Wilder et al. | |
| 3,762,400 A | 10/1973 | McDonald | |
| 3,769,968 A | 11/1973 | Blount et al. | |
| 3,789,835 A | 2/1974 | Whitman | |
| 3,815,585 A | 6/1974 | Fiore | |
| 3,826,248 A * | 7/1974 | Gobels | A61B 1/267 600/199 |
| 3,851,642 A * | 12/1974 | McDonald | A61M 29/02 600/223 |
| 3,919,541 A | 11/1975 | Chao | |
| 3,934,578 A | 1/1976 | Heine | |
| 3,945,371 A | 3/1976 | Adelman | |
| 3,978,850 A * | 9/1976 | Moore | A61B 1/227 600/249 |
| 4,067,323 A | 1/1978 | Troutner | |
| 4,156,424 A | 5/1979 | Burgin | |
| 4,210,133 A | 7/1980 | Castaneda | |
| 4,226,228 A | 10/1980 | Shin et al. | |
| 4,263,899 A | 4/1981 | Burgin | |
| 4,300,541 A | 11/1981 | Burgin | |
| 4,337,763 A * | 7/1982 | Petrassevich | A61B 1/0676 600/245 |
| 4,432,351 A | 2/1984 | Hoary | |
| 4,492,220 A | 1/1985 | Hayes | |
| 4,502,468 A | 3/1985 | Burgin | |
| 4,527,553 A | 7/1985 | Upsher | |
| 4,546,761 A | 10/1985 | McCullough | |
| 4,551,129 A | 11/1985 | Coleman et al. | |
| 4,562,832 A | 1/1986 | Wilder | |
| 4,566,439 A | 1/1986 | Burgin | |
| 4,574,784 A * | 3/1986 | Soloway | A61B 1/267 600/199 |
| 4,596,239 A | 6/1986 | Bauman | |
| 4,597,383 A | 7/1986 | Van Der Bel | |
| 4,607,623 A | 8/1986 | Bauman | |
| 4,619,248 A | 10/1986 | Walsh | |
| 4,638,792 A | 1/1987 | Burgin | |
| 4,759,349 A | 7/1988 | Betz et al. | |
| 4,766,887 A | 8/1988 | Cecil, Jr. et al. | |
| 4,807,600 A | 2/1989 | Hayes | |
| 4,884,559 A | 12/1989 | Collins | |
| 4,901,708 A | 2/1990 | Lee | |
| 4,905,670 A | 3/1990 | Adair | |
| 4,934,352 A | 6/1990 | Sullivan, Jr. | |
| 4,971,036 A * | 11/1990 | Collins | A61B 1/32 600/220 |
| 5,018,507 A | 5/1991 | Montaldi | |
| 5,026,368 A | 6/1991 | Adair | |
| 5,054,906 A | 10/1991 | Lyons, Jr. | |
| 5,063,908 A | 11/1991 | Collins | |
| 5,143,054 A | 9/1992 | Adair | |
| 5,165,387 A | 11/1992 | Woodson | |
| 5,174,278 A | 12/1992 | Babkow | |
| 5,179,937 A | 1/1993 | Lee | |
| 5,179,938 A | 1/1993 | Lonky | |
| 5,211,468 A | 5/1993 | Jeng | |
| 5,222,271 A | 6/1993 | Eganhouse | |
| D337,384 S | 7/1993 | Schucman | |
| 5,231,973 A | 8/1993 | Dickie | |
| 5,318,009 A | 6/1994 | Robinson | |
| 5,329,938 A | 7/1994 | Lonky | |
| 5,427,152 A | 6/1995 | Weber | |
| 5,438,976 A | 8/1995 | Nash | |
| 5,465,709 A | 11/1995 | Dickie et al. | |
| 5,499,964 A | 3/1996 | Beck et al. | |
| 5,512,038 A | 4/1996 | O'Neal et al. | |
| 5,553,627 A | 9/1996 | Newkirk | |
| 5,695,492 A | 12/1997 | Brown | |
| 5,716,329 A | 2/1998 | Dieter | |
| 5,785,408 A | 7/1998 | Tseng | |
| 5,785,648 A | 7/1998 | Min | |
| 5,840,013 A | 11/1998 | Lee et al. | |
| 5,846,249 A | 12/1998 | Thompson | |
| 5,865,729 A | 2/1999 | Meehan | |
| 5,873,820 A | 2/1999 | Norell | |
| 5,879,304 A | 3/1999 | Schuchman et al. | |
| 5,888,195 A | 3/1999 | Schneider | |
| 5,899,854 A | 5/1999 | Slishman | |
| 5,902,315 A | 5/1999 | Dubois | |
| 5,916,150 A | 6/1999 | Sillman | |
| 5,951,142 A | 9/1999 | Wang et al. | |
| 5,967,971 A | 10/1999 | Bolser | |
| 6,001,077 A | 12/1999 | Ellman et al. | |
| 6,004,265 A | 12/1999 | Hsu et al. | |
| 6,036,638 A | 3/2000 | Nwawka | |
| 6,036,713 A | 3/2000 | Kieturakis | |
| 6,048,308 A | 4/2000 | Strong | |
| 6,080,105 A | 6/2000 | Spears | |
| 6,116,747 A | 9/2000 | Grawemeyer et al. | |
| 6,130,520 A | 10/2000 | Wawro et al. | |
| 6,176,824 B1 | 1/2001 | Davis | |
| 6,186,638 B1 | 2/2001 | Chang | |
| 6,186,944 B1 | 2/2001 | Tsai | |
| 6,193,653 B1 | 2/2001 | Evans et al. | |
| 6,217,512 B1 | 4/2001 | Salo et al. | |
| 6,231,505 B1 | 5/2001 | Martin | |
| 6,231,506 B1 | 5/2001 | Hu et al. | |
| 6,254,247 B1 | 7/2001 | Carson | |
| 6,277,067 B1 | 8/2001 | Blair | |
| 6,319,199 B1 | 11/2001 | Sheehan et al. | |
| 6,346,085 B1 | 2/2002 | Schiffman | |

(56) References Cited

U.S. PATENT DOCUMENTS

| | | |
|---|---|---|
| 6,359,644 B1 | 3/2002 | Salvati |
| 6,361,489 B1 | 3/2002 | Tsai |
| 6,363,763 B1 | 4/2002 | Geringer et al. |
| 6,379,296 B1 | 4/2002 | Baggett |
| 6,379,299 B1 | 4/2002 | Borodulin et al. |
| 6,394,111 B1 | 5/2002 | Jacobs et al. |
| 6,394,950 B1 | 5/2002 | Weiss |
| 6,413,208 B1 | 7/2002 | Schöllhauser et al. |
| 6,416,465 B2 | 7/2002 | Brau |
| 6,428,180 B1 | 8/2002 | Karram et al. |
| 6,432,045 B2 | 8/2002 | Lemperle et al. |
| 6,432,049 B1 | 8/2002 | Banta |
| 6,436,033 B2 | 8/2002 | Tan |
| 6,450,952 B1 | 9/2002 | Rioux |
| 6,468,206 B1 | 10/2002 | Hipps et al. |
| 6,468,232 B1 | 10/2002 | Ashton-Miller et al. |
| 6,487,440 B2 | 11/2002 | Deckert et al. |
| 6,504,985 B2 | 1/2003 | Parker et al. |
| 6,523,973 B2 | 2/2003 | Galli |
| 6,524,259 B2 | 2/2003 | Baxter-Jones et al. |
| 6,569,089 B1 | 5/2003 | Covington et al. |
| 6,569,091 B2 | 5/2003 | Diokno et al. |
| 6,589,168 B2 | 7/2003 | Thompson |
| 6,595,917 B2 | 7/2003 | Nieto |
| 6,616,603 B1 | 9/2003 | Fontana |
| 6,626,825 B2 | 9/2003 | Tsai |
| 6,663,576 B2 | 12/2003 | Gombrich et al. |
| 6,676,598 B2 | 1/2004 | Rudischhauser et al. |
| 6,719,688 B2 | 4/2004 | Pecherer et al. |
| 6,761,687 B1 | 7/2004 | Doshi |
| 6,830,547 B2 | 12/2004 | Weiss |
| 6,896,653 B1 | 5/2005 | Vail, III et al. |
| 7,014,340 B2 | 3/2006 | Betis |
| 7,029,439 B2 | 4/2006 | Roberts et al. |
| D520,464 S | 5/2006 | Strong |
| 7,066,615 B2 | 6/2006 | Diggle, III et al. |
| 7,223,223 B2 | 5/2007 | Lindsay |
| 7,276,025 B2 | 10/2007 | Roberts et al. |
| 7,306,559 B2 | 12/2007 | Williams |
| 7,474,820 B2 | 1/2009 | Vayser et al. |
| 7,492,116 B2 | 2/2009 | Oleynikov et al. |
| 7,510,524 B2 | 3/2009 | Vayser et al. |
| 7,631,981 B2 | 12/2009 | Miller et al. |
| 7,736,304 B2 | 6/2010 | Pecherer |
| 7,758,203 B2 | 7/2010 | McMahon et al. |
| 7,845,824 B2 | 12/2010 | Robotham |
| 7,878,973 B2 | 2/2011 | Yee et al. |
| 7,901,353 B2 | 3/2011 | Vayser et al. |
| 7,909,759 B2 | 3/2011 | Pecherer |
| 7,967,809 B2 | 6/2011 | Jay-Robinson |
| 8,012,089 B2 | 9/2011 | Bayat |
| 8,047,987 B2 | 11/2011 | Grey et al. |
| 8,052,702 B2 | 11/2011 | Hess et al. |
| 8,088,066 B2 | 1/2012 | Grey et al. |
| 8,096,945 B2 | 1/2012 | Buchok et al. |
| 8,142,352 B2 | 3/2012 | Vivenzio et al. |
| 8,142,353 B2 | 3/2012 | Pecherer et al. |
| 8,157,728 B2 | 4/2012 | Danna et al. |
| 8,162,824 B2 | 4/2012 | Vayser et al. |
| 8,162,826 B2 | 4/2012 | Pecherer et al. |
| 8,251,898 B2 | 8/2012 | Pecherer |
| 8,285,093 B2 | 10/2012 | Vayser et al. |
| 8,292,805 B2 | 10/2012 | Vayser et al. |
| 8,317,693 B2 | 11/2012 | Grey et al. |
| 8,376,942 B2 | 2/2013 | Krauter et al. |
| 8,388,523 B2 | 3/2013 | Vivenzio et al. |
| 8,394,016 B1 | 3/2013 | Arne |
| 8,394,017 B2 | 3/2013 | Kieffer |
| 8,435,175 B2 | 5/2013 | McMahon et al. |
| 8,459,844 B2 | 6/2013 | Lia et al. |
| 8,512,234 B2 | 8/2013 | Grey et al. |
| 8,512,237 B2 | 8/2013 | Bastia |
| 8,555,892 B2 | 10/2013 | Traub |
| 8,594,472 B2 | 11/2013 | Vayser et al. |
| 8,596,847 B2 | 12/2013 | Vayser et al. |
| 8,628,879 B2 | 1/2014 | Pecherer et al. |
| 8,651,704 B1 | 2/2014 | Gordin et al. |
| 8,708,896 B2 | 4/2014 | Vayser et al. |
| 8,758,342 B2 * | 6/2014 | Bales ................. A61B 18/1445 606/51 |
| 8,786,210 B2 | 7/2014 | Delucia |
| 8,795,162 B2 | 8/2014 | Vayser et al. |
| 8,821,385 B2 | 9/2014 | Naito |
| 8,870,761 B2 | 10/2014 | Vayser et al. |
| 8,890,489 B2 | 11/2014 | Wood |
| D719,652 S | 12/2014 | Swift |
| 8,899,809 B2 | 12/2014 | Vayser et al. |
| 8,979,745 B2 | 3/2015 | Swift |
| 9,002,159 B2 | 4/2015 | Sutherland et al. |
| 9,005,115 B2 | 4/2015 | Vayser |
| 9,044,161 B2 | 6/2015 | Vayser et al. |
| 9,050,048 B2 | 6/2015 | Nadershahi |
| 9,072,452 B2 | 7/2015 | Vayser et al. |
| 9,072,455 B2 | 7/2015 | Vayser et al. |
| D745,669 S | 12/2015 | Swift |
| 9,198,566 B2 | 12/2015 | Lia et al. |
| 9,229,165 B2 | 1/2016 | Vayser et al. |
| 9,241,617 B2 | 1/2016 | Grey et al. |
| D752,217 S | 3/2016 | Swift |
| 9,271,709 B2 | 3/2016 | Grey et al. |
| 9,271,710 B2 | 3/2016 | Grey et al. |
| 9,282,878 B2 | 3/2016 | Grey et al. |
| D753,295 S | 4/2016 | Vivenzio et al. |
| 9,307,897 B2 * | 4/2016 | Swift ....................... A61B 1/32 |
| 9,308,054 B2 | 4/2016 | Vayser et al. |
| 9,326,812 B2 * | 5/2016 | Waaler ............... A61B 18/1442 |
| 9,332,898 B2 | 5/2016 | McMahon et al. |
| 9,386,913 B2 * | 7/2016 | Holland .................. A61B 1/32 |
| 9,429,746 B2 | 8/2016 | Vayser et al. |
| 9,468,366 B2 | 10/2016 | Grey et al. |
| 9,504,373 B2 | 11/2016 | Vayser et al. |
| 9,510,737 B2 | 12/2016 | Vayser et al. |
| 9,532,706 B2 | 1/2017 | McMahon et al. |
| 9,574,742 B2 | 2/2017 | Vayser et al. |
| 9,629,529 B1 | 4/2017 | Indovina et al. |
| 9,636,004 B2 | 5/2017 | Lia et al. |
| 9,636,182 B2 | 5/2017 | Vayser et al. |
| 9,718,130 B1 | 8/2017 | Vayser et al. |
| 9,763,743 B2 | 9/2017 | Lin et al. |
| 9,808,231 B2 | 11/2017 | Miraki et al. |
| 9,814,377 B2 | 11/2017 | Lia et al. |
| 9,820,638 B2 | 11/2017 | Cheng |
| 9,820,729 B2 | 11/2017 | Miles et al. |
| 9,826,892 B2 | 11/2017 | Dresher et al. |
| 9,833,295 B2 | 12/2017 | Vayser et al. |
| 9,833,308 B2 | 12/2017 | Dye |
| 9,844,364 B2 | 12/2017 | Grey et al. |
| 9,861,349 B2 | 1/2018 | Nadershahi et al. |
| 9,867,531 B2 | 1/2018 | Pacey et al. |
| 9,867,602 B2 | 1/2018 | Swift |
| 9,877,639 B2 | 1/2018 | Grey et al. |
| 9,877,644 B2 | 1/2018 | Greenstein et al. |
| D809,660 S | 2/2018 | Nguyen et al. |
| 9,883,792 B2 | 2/2018 | McMahon et al. |
| 9,888,957 B2 | 2/2018 | Wolf et al. |
| 9,907,544 B2 | 3/2018 | Nadershahi et al. |
| 9,913,682 B2 | 3/2018 | Wolf et al. |
| 9,914,202 B2 | 3/2018 | Portaro |
| 9,918,618 B2 | 3/2018 | Molnar |
| 9,918,802 B2 | 3/2018 | Coppersmith et al. |
| 9,931,028 B2 | 4/2018 | Lia et al. |
| 9,943,295 B2 | 4/2018 | King |
| 9,949,814 B2 | 4/2018 | Alexander et al. |
| 9,955,858 B2 | 5/2018 | Pamnani et al. |
| 9,968,262 B2 | 5/2018 | Greenstein et al. |
| 9,968,346 B2 | 5/2018 | Alexander et al. |
| 9,980,710 B2 | 5/2018 | Seifert et al. |
| 9,986,901 B2 | 6/2018 | Grey et al. |
| 9,986,903 B2 | 6/2018 | Nadershahi et al. |
| 9,986,988 B2 | 6/2018 | Ferro et al. |
| 9,999,345 B2 | 6/2018 | Vayser et al. |
| 10,004,392 B2 | 6/2018 | Millard et al. |
| 10,004,393 B2 | 6/2018 | Kucklick |
| 10,028,648 B2 | 7/2018 | Goldfain et al. |

(56) References Cited

U.S. PATENT DOCUMENTS

| | | | |
|---|---|---|---|
| 10,028,649 B2 | 7/2018 | Salvati et al. |
| 10,028,780 B2 | 7/2018 | Wolf et al. |
| 10,045,686 B2 | 8/2018 | Yang et al. |
| 10,045,731 B2 | 8/2018 | Prasad et al. |
| 10,052,432 B2 | 8/2018 | Dexter et al. |
| 10,064,611 B2 | 9/2018 | Ross et al. |
| 10,064,613 B2 | 9/2018 | Davis et al. |
| 10,068,173 B2 | 9/2018 | Vayser et al. |
| 10,092,176 B2 | 10/2018 | Kienzle et al. |
| 10,092,281 B2 | 10/2018 | Perler et al. |
| 10,098,530 B2 | 10/2018 | McMahon et al. |
| 10,105,043 B2 | 10/2018 | George |
| 10,117,646 B2 | 11/2018 | Friedrich et al. |
| 10,130,441 B2 | 11/2018 | Martinez |
| 10,166,016 B2 | 1/2019 | Shimizu et al. |
| 10,172,601 B2 | 1/2019 | Ahn |
| 10,174,933 B2 | 1/2019 | Phillips, Jr. et al. |
| 10,188,298 B2 | 1/2019 | Greenstein et al. |
| 10,213,271 B2 | 2/2019 | Duggal et al. |
| 10,219,800 B2 | 3/2019 | Tsubouchi |
| 10,220,445 B2 | 3/2019 | Vayser et al. |
| 10,226,555 B2 | 3/2019 | Vayser et al. |
| 10,238,462 B2 | 3/2019 | Wood et al. |
| D846,119 S | 4/2019 | Greeley et al. |
| 10,278,571 B2 | 5/2019 | Poormand |
| 10,292,782 B2 | 5/2019 | Haverich et al. |
| 10,292,784 B2 | 5/2019 | Duggal et al. |
| 10,321,969 B2 | 6/2019 | Wayne et al. |
| 10,342,525 B2 | 7/2019 | Wilson |
| 10,456,190 B2 | 10/2019 | Vayser et al. |
| 10,499,974 B2 | 12/2019 | Heim et al. |
| 10,500,010 B2 | 12/2019 | Vayser et al. |
| 10,512,518 B2 | 12/2019 | Vayser et al. |
| 10,512,520 B2 | 12/2019 | Wayne et al. |
| 10,531,933 B2 | 1/2020 | Vayser et al. |
| 10,548,682 B2 | 2/2020 | Vayser et al. |
| 10,568,712 B2 | 2/2020 | Vayser et al. |
| 10,601,004 B2* | 3/2020 | Lindemann ......... H01M 50/247 |
| 10,675,115 B2 | 6/2020 | Vayser et al. |
| 10,729,511 B2 | 8/2020 | Vayser et al. |
| 10,729,512 B2 | 8/2020 | Wayne et al. |
| 2001/0029044 A1 | 10/2001 | Gombrich et al. |
| 2002/0009275 A1 | 1/2002 | Williams et al. |
| 2002/0016528 A1 | 2/2002 | Tan |
| 2002/0022769 A1 | 2/2002 | Smith et al. |
| 2002/0038075 A1 | 3/2002 | Tsai |
| 2002/0038076 A1 | 3/2002 | Sheehan et al. |
| 2002/0055670 A1 | 5/2002 | Weiss |
| 2002/0076607 A1* | 6/2002 | Chang ................ H01M 50/00 |
| | | 429/97 |
| 2002/0115909 A1 | 8/2002 | Bolser |
| 2002/0156350 A1 | 10/2002 | Nieto |
| 2002/0165435 A1 | 11/2002 | Weiss |
| 2002/0198471 A1 | 12/2002 | Baxter-Jones et al. |
| 2003/0095781 A1 | 5/2003 | Willaims |
| 2003/0105387 A1 | 6/2003 | Frumovitz et al. |
| 2003/0139673 A1 | 7/2003 | Vivenzio et al. |
| 2003/0158502 A1 | 8/2003 | Baxter-Jones et al. |
| 2003/0176772 A1* | 9/2003 | Yang ...................... A61B 1/32 |
| | | 600/220 |
| 2003/0187331 A1 | 10/2003 | Faludi et al. |
| 2004/0026829 A1 | 2/2004 | Van Der Weegen |
| 2004/0054260 A1 | 3/2004 | Klaassen et al. |
| 2004/0141175 A1 | 7/2004 | Baldwin et al. |
| 2004/0183482 A1 | 9/2004 | Roberts et al. |
| 2004/0184288 A1 | 9/2004 | Bettis |
| 2004/0186355 A1 | 9/2004 | Strong |
| 2004/0254428 A1 | 12/2004 | Ritland |
| 2005/0065496 A1 | 3/2005 | Simon et al. |
| 2005/0085699 A1 | 4/2005 | Weiss |
| 2005/0085723 A1 | 4/2005 | Huebner |
| 2005/0093718 A1 | 5/2005 | Martin |
| 2005/0125015 A1 | 6/2005 | McNally-Heintzelman et al. |
| 2005/0159649 A1 | 7/2005 | Patel |
| 2005/0182301 A1 | 8/2005 | Acker et al. |
| 2005/0192482 A1 | 9/2005 | Carpenter |
| 2005/0215858 A1 | 9/2005 | Vail, III |
| 2005/0240081 A1 | 10/2005 | Eliachar |
| 2005/0277811 A1 | 12/2005 | Richards et al. |
| 2006/0084843 A1 | 4/2006 | Sommerich et al. |
| 2006/0122463 A1 | 6/2006 | Klassen et al. |
| 2006/0155276 A1 | 7/2006 | Walulik et al. |
| 2006/0189847 A1 | 8/2006 | Yee et al. |
| 2006/0200186 A1 | 9/2006 | Marchek et al. |
| 2006/0291195 A1 | 12/2006 | Horrell et al. |
| 2007/0043264 A1 | 2/2007 | Gillis et al. |
| 2007/0060795 A1 | 3/2007 | Vayser et al. |
| 2007/0060938 A1 | 3/2007 | Dziadik et al. |
| 2007/0066872 A1 | 3/2007 | Morrison et al. |
| 2007/0093693 A1 | 4/2007 | Geist et al. |
| 2007/0100212 A1 | 5/2007 | Pimenta et al. |
| 2007/0179342 A1 | 8/2007 | Miller et al. |
| 2007/0208226 A1 | 9/2007 | Grey et al. |
| 2007/0230164 A1 | 10/2007 | Vivenzio et al. |
| 2007/0230167 A1 | 10/2007 | McMahon et al. |
| 2007/0255110 A1 | 11/2007 | Wax et al. |
| 2007/0270866 A1 | 11/2007 | Von Jako |
| 2007/0287888 A1 | 12/2007 | Lovell et al. |
| 2008/0002426 A1 | 1/2008 | Vayser et al. |
| 2008/0027461 A1 | 1/2008 | Vaquero et al. |
| 2008/0108877 A1 | 5/2008 | Bayat |
| 2008/0113312 A1 | 5/2008 | Ortega |
| 2008/0221569 A1 | 9/2008 | Moore et al. |
| 2008/0228038 A1 | 9/2008 | McMahon et al. |
| 2008/0269564 A1 | 10/2008 | Gelnett |
| 2008/0269565 A1 | 10/2008 | McMahon et al. |
| 2008/0278936 A1 | 11/2008 | Kurth et al. |
| 2009/0018400 A1 | 1/2009 | Raymond et al. |
| 2009/0069634 A1 | 3/2009 | Larkin |
| 2009/0097236 A1 | 4/2009 | Miller et al. |
| 2009/0112068 A1 | 4/2009 | Grey et al. |
| 2009/0209816 A1 | 8/2009 | Gunther et al. |
| 2009/0240245 A1* | 9/2009 | Deville ............... A61B 18/1445 |
| | | 606/33 |
| 2009/0275803 A1 | 11/2009 | Krauter et al. |
| 2009/0287192 A1 | 11/2009 | Vivenzio et al. |
| 2009/0312610 A1 | 12/2009 | Buchok et al. |
| 2010/0036382 A1 | 2/2010 | Bonnadier |
| 2010/0041955 A1 | 2/2010 | Grey et al. |
| 2010/0097794 A1 | 4/2010 | Teng et al. |
| 2010/0190129 A1 | 7/2010 | Paz |
| 2010/0191062 A1 | 7/2010 | Kieffer |
| 2010/0249513 A1 | 9/2010 | Tydlaska |
| 2010/0261967 A1 | 10/2010 | Pacey et al. |
| 2010/0292533 A1 | 11/2010 | Kasahara et al. |
| 2011/0022032 A1 | 1/2011 | Zemlok et al. |
| 2011/0130632 A1 | 6/2011 | McGrail et al. |
| 2011/0257650 A1 | 10/2011 | Deville et al. |
| 2011/0275894 A1 | 11/2011 | Mackin |
| 2012/0055470 A1 | 3/2012 | Pecherer et al. |
| 2012/0059226 A1 | 3/2012 | Funt |
| 2012/0078060 A1 | 3/2012 | Swift |
| 2012/0116170 A1 | 5/2012 | Vayser et al. |
| 2012/0232352 A1 | 9/2012 | Lin et al. |
| 2012/0243212 A1 | 9/2012 | Smith et al. |
| 2012/0277780 A1 | 11/2012 | Smith et al. |
| 2012/0330103 A1 | 12/2012 | Tenger et al. |
| 2013/0018230 A1 | 1/2013 | Su et al. |
| 2013/0021798 A1 | 1/2013 | Chen et al. |
| 2013/0041229 A2 | 2/2013 | Hahn et al. |
| 2013/0046290 A1 | 2/2013 | Palmer et al. |
| 2013/0092421 A1 | 4/2013 | Kajiya |
| 2013/0102850 A1 | 4/2013 | Fiorella |
| 2013/0102887 A1 | 4/2013 | Thompson et al. |
| 2013/0109910 A1 | 5/2013 | Alexander et al. |
| 2013/0158345 A1 | 6/2013 | Majlessi |
| 2013/0197313 A1* | 8/2013 | Wan ..................... A61B 90/36 |
| | | 600/245 |
| 2013/0226198 A1 | 8/2013 | Kamler |
| 2013/0245381 A1 | 9/2013 | Dang et al. |
| 2013/0245657 A1 | 9/2013 | Deville et al. |
| 2013/0267786 A1 | 10/2013 | Vayser et al. |
| 2013/0281784 A1 | 10/2013 | Ray |
| 2013/0324801 A1 | 12/2013 | Grey et al. |

(56) References Cited

U.S. PATENT DOCUMENTS

| | | |
|---|---|---|
| 2014/0088371 A1 | 3/2014 | Vayser et al. |
| 2014/0179998 A1 | 6/2014 | Pacey |
| 2014/0202459 A1 | 7/2014 | Iqbal |
| 2014/0228875 A1 | 8/2014 | Saadat |
| 2014/0257039 A1 | 9/2014 | Feldman |
| 2014/0275790 A1 | 9/2014 | Vivenzio et al. |
| 2014/0309499 A1 | 10/2014 | Swift |
| 2014/0316211 A1 | 10/2014 | Hermle |
| 2014/0323800 A1 | 10/2014 | Dye |
| 2014/0323811 A1 | 10/2014 | DeSantis et al. |
| 2014/0364695 A1 | 12/2014 | Nadershahi et al. |
| 2014/0371536 A1 | 12/2014 | Miller et al. |
| 2015/0018625 A1 | 1/2015 | Miraki et al. |
| 2015/0141866 A1 | 5/2015 | Mayse et al. |
| 2015/0157387 A1 | 6/2015 | Ouyang et al. |
| 2015/0157469 A1 | 6/2015 | Prado et al. |
| 2015/0238070 A1 | 8/2015 | Lia et al. |
| 2015/0285382 A1 | 10/2015 | Kienreich et al. |
| 2015/0289757 A1 | 10/2015 | Swift |
| 2015/0297217 A1 | 10/2015 | Huitema et al. |
| 2016/0000305 A1 | 1/2016 | Elbaz et al. |
| 2016/0030128 A1 | 2/2016 | Duggal et al. |
| 2016/0038032 A1 | 2/2016 | Dan |
| 2016/0066915 A1 | 3/2016 | Baber et al. |
| 2016/0081833 A1 | 3/2016 | Leblanc et al. |
| 2016/0095506 A1 | 4/2016 | Dan et al. |
| 2016/0100751 A1 | 4/2016 | Davis et al. |
| 2016/0151058 A1 | 6/2016 | Ferro et al. |
| 2016/0242637 A1 | 8/2016 | Tydlaska et al. |
| 2016/0302657 A1 | 10/2016 | Hussey et al. |
| 2016/0310121 A1 | 10/2016 | Swift |
| 2017/0007228 A1 | 1/2017 | Costabile |
| 2017/0020621 A1 | 1/2017 | Huldin et al. |
| 2017/0059400 A1 | 3/2017 | Murphy et al. |
| 2017/0065282 A1 | 3/2017 | Mathis et al. |
| 2017/0079518 A1 | 3/2017 | Elbaz et al. |
| 2017/0172404 A1 | 6/2017 | McMahon et al. |
| 2017/0172555 A1 | 6/2017 | Shimizu et al. |
| 2017/0181605 A1 | 6/2017 | Lalli et al. |
| 2017/0181607 A1 | 6/2017 | Lalli et al. |
| 2017/0181615 A1 | 6/2017 | Vella et al. |
| 2017/0181616 A1 | 6/2017 | Vella et al. |
| 2017/0224206 A1 | 8/2017 | Vayser |
| 2017/0231712 A1 | 8/2017 | Vayser |
| 2017/0296162 A1 | 10/2017 | Wan |
| 2017/0300623 A1 | 10/2017 | Rosenblatt et al. |
| 2017/0303903 A1 | 10/2017 | De Koning et al. |
| 2017/0347871 A1 | 12/2017 | Wallace et al. |
| 2017/0360423 A1 | 12/2017 | Stevenson et al. |
| 2018/0000469 A1 | 1/2018 | Wood et al. |
| 2018/0008137 A1 | 1/2018 | Poormand |
| 2018/0008138 A1 | 1/2018 | Thommen et al. |
| 2018/0008368 A1 | 1/2018 | Duggal et al. |
| 2018/0014721 A1 | 1/2018 | Rullo et al. |
| 2018/0014842 A1 | 1/2018 | Shener-Irmakoglu |
| 2018/0014900 A1 | 1/2018 | Vayser et al. |
| 2018/0021100 A1 | 1/2018 | Swift |
| 2018/0036031 A1 | 2/2018 | Smith et al. |
| 2018/0036095 A1 | 2/2018 | Vayser et al. |
| 2018/0042596 A1 | 2/2018 | Tsubouchi |
| 2018/0064316 A1 | 3/2018 | Charles et al. |
| 2018/0064317 A1 | 3/2018 | Tesar |
| 2018/0078301 A1 | 3/2018 | Vayser |
| 2018/0116581 A1 | 5/2018 | Prasad et al. |
| 2018/0125336 A1 | 5/2018 | Goldfarb et al. |
| 2018/0125347 A1 | 5/2018 | Czyzewski et al. |
| 2018/0132710 A1 | 5/2018 | Pacey et al. |
| 2018/0132970 A1 | 5/2018 | Ritter |
| 2018/0153391 A1 | 6/2018 | McMahon et al. |
| 2018/0156448 A1 | 6/2018 | Phillips, Jr. et al. |
| 2018/0206832 A1 | 7/2018 | Greeley et al. |
| 2018/0228376 A1 | 8/2018 | Greenstein et al. |
| 2018/0228483 A1 | 8/2018 | Duggal et al. |
| 2018/0235444 A1 | 8/2018 | Tsai |
| 2018/0235592 A1 | 8/2018 | Kass et al. |
| 2018/0249902 A1 | 9/2018 | Grey et al. |
| 2018/0263480 A1 | 9/2018 | Lalli et al. |
| 2018/0263481 A1 | 9/2018 | Muratori et al. |
| 2018/0271581 A1 | 9/2018 | Yang et al. |
| 2018/0280011 A1 | 10/2018 | Ferro et al. |
| 2018/0296082 A1 | 10/2018 | Salvati et al. |
| 2018/0296204 A1 | 10/2018 | Davis |
| 2018/0317746 A1 | 11/2018 | Lalli et al. |
| 2018/0317752 A1 | 11/2018 | Cybulski et al. |
| 2018/0317902 A1 | 11/2018 | Green et al. |
| 2018/0328572 A1 | 11/2018 | Kennedy et al. |
| 2019/0038273 A1 | 2/2019 | Perler et al. |
| 2019/0049655 A1 | 2/2019 | Zagatsky et al. |
| 2019/0076138 A1 | 3/2019 | Opperman |
| 2019/0083079 A1 | 3/2019 | Shimizu et al. |
| 2019/0133432 A1 | 5/2019 | Tsai |
| 2019/0143006 A1 | 5/2019 | Vayser et al. |
| 2019/0143414 A1 | 5/2019 | Vayser et al. |
| 2019/0150422 A1 | 5/2019 | Welch |
| 2019/0150725 A1 | 5/2019 | Ramanujam et al. |
| 2019/0150739 A1 | 5/2019 | Wawro et al. |
| 2019/0150786 A1 | 5/2019 | Vassallo et al. |
| 2019/0167111 A1 | 6/2019 | Greenstein et al. |
| 2019/0167378 A1 | 6/2019 | Wood et al. |
| 2019/0190293 A1 | 6/2019 | Wawro et al. |
| 2019/0223708 A1 | 7/2019 | Recanati et al. |
| 2019/0254512 A1 | 8/2019 | Spiertz |
| 2019/0254771 A1 | 8/2019 | Swift et al. |
| 2019/0335988 A1 | 11/2019 | Lia et al. |
| 2019/0343379 A1 | 11/2019 | Altamura |
| 2019/0365217 A1 | 12/2019 | Hegenberger |
| 2020/0008694 A1 | 1/2020 | Karla et al. |
| 2020/0046216 A1 | 2/2020 | Moein |
| 2020/0069171 A1 | 3/2020 | Miller et al. |
| 2020/0107714 A1 | 4/2020 | Bar-Or et al. |
| 2020/0253467 A1 | 8/2020 | Lees, Jr. et al. |
| 2020/0337541 A1 | 10/2020 | Vivenzio et al. |
| 2021/0145270 A1 | 5/2021 | Altamura |

FOREIGN PATENT DOCUMENTS

| | | |
|---|---|---|
| CN | 2516109 Y | 10/2002 |
| CN | 2629738 Y | 8/2004 |
| CN | 1565664 A | 1/2005 |
| CN | 2668152 | 1/2005 |
| CN | 2668152 Y | 1/2005 |
| CN | 1717195 A | 1/2006 |
| CN | 101179982 A | 5/2008 |
| CN | 201055387 Y | 5/2008 |
| CN | 203591245 U | 5/2008 |
| CN | 201139589 Y | 10/2008 |
| CN | 102415869 A | 4/2012 |
| CN | 103154793 A | 6/2013 |
| CN | 302536685 S | 8/2013 |
| CN | 103925266 A | 7/2014 |
| CN | 203898367 U | 10/2014 |
| CN | 102573700 B | 12/2014 |
| DE | 2128855 A | 12/1972 |
| DE | 10216618 A1 | 1/2003 |
| DE | 202004002963 U1 | 5/2004 |
| DE | 102005002220 A1 | 10/2005 |
| DE | 202005019780 U1 | 5/2006 |
| DE | 600 33 612 T2 | 12/2007 |
| DE | 202010001 7638 U | 5/2012 |
| EP | 0190014 A3 | 8/1986 |
| EP | 1074224 A2 | 7/2001 |
| FR | 2490478 A1 | 3/1982 |
| GB | 2505463 A | 5/2014 |
| RU | 2187972 C2 | 8/2002 |
| RU | 2308873 C2 | 10/2007 |
| WO | 9825512 A1 | 6/1998 |
| WO | 0137739 A1 | 5/2001 |
| WO | 01/62137 A2 | 8/2001 |
| WO | 03082123 A2 | 10/2003 |
| WO | 2004064624 A1 | 8/2004 |
| WO | 2006107877 A2 | 10/2006 |
| WO | 2006107878 A2 | 10/2006 |
| WO | 2007/084641 A2 | 7/2007 |
| WO | 2009/090383 A2 | 7/2009 |

(56) References Cited

FOREIGN PATENT DOCUMENTS

| WO | 2009137017 A2 | 11/2009 |
| WO | 2013-044151 A1 | 3/2013 |
| WO | 2014-041172 A1 | 3/2014 |
| WO | 2015/164881 A1 | 10/2015 |
| WO | 2006121530 A2 | 11/2016 |
| WO | 2016196788 A1 | 12/2016 |

OTHER PUBLICATIONS

International Search Report for International application No. PCT/US2021/014076 issued Apr. 15, 2021, a copy of which is enclosed.
International Search Report for International application No. PCT/US2016/016154 issued May 19, 2016 for corresponding U.S. application, U.S. Appl. No. 14/614,413, a copy of which is enclosed.
International Search Report, for International application No. PCT/US2016/035508 issued Sep. 15, 2016 for corresponding U.S. application, U.S. Appl. No. 15/171,581, a copy of which is enclosed.
International Search Report for International application No. PCT/US2016/036833 issued Jan. 19, 2017.
U.S. Patent references 121-125 and U.S. Published Patent Application references 48 and 50 were cited in an Office Action issued in U.S. Appl. No. 15/171,581, a copy of which is enclosed.
U.S. Published Patent Application references 47, 49 and 51 were cited in a PCT Search Report issued in PCT Application No. PCT/US2017/042617, a copy of which is enclosed.
The above foreign patent documents 18, 21, 22, 23 and 24 were cited in a Nov. 1, 2017 Chinese Office Action, a copy of which is enclosed without an English Translation, that issued in Chinese Patent Application No. 201510543086.7.
The above foreign patent documents 21, 22 and 26 was cited in the Jul. 16, 2018 Chinese Office Action, a copy of which is enclosed without an English Translation, that issued in Chinese Patent Application No. 201510543086.7.
Solvey, Techinical Data Sheet, Ixef 1022 polyarylamide, Feb. 13, 2015, pp. 1-5.
http://www.makeitfrom.com/material-properties/Polyetheretheketone-PEEK, printed on Oct. 9, 2016, pp. 1-9.
https://web.archive.org/web/20160618175418/http://bihlermed.com:80/scintillant/; Home—Scintillant® Surgical Light : Scintillant® Surgical Light; printed Oct. 19, 2022 (One Page).
European Search Report issued on Nov. 23, 2018, a copy of which is enclosed, that issued in the corresponding European Patent Application No. 16747107.7.
Oct. 29, 2018 Chinese Office Action, a copy of which is enclosed without an English Translation, that issued in Chinese Patent Application No. 201711159829.6.
International Search Report of PCT/US2018/054925, Oct. 9, 2018, a copy of which is enclosed.
Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.
The above U.S. Publications documents #1 and #2 were cited in a Supplementary European Search Report issued on Apr. 24, 2019, a copy of which is enclosed, that issued in European Patent Application No. 16804432.9.
OBP Medical—OfficeSPEC, Premier Speculum for In-Office Procedures published Nov. 30, 2009 (1 page).
OBP Medical—ER-SPEC OBGYN Brochure published Nov. 19, 2014 (2 pages).
OBP Medical—ER-SPEC Brochure, Light Source Now 10× Brighter published Oct. 30, 2012 (1 page).
OBP Medical—ER-SPEC Product Presentation published Apr. 16, 2014 (12 pages).
OBP Medical—ER-SPEC Brochure published Apr. 11, 2013 (2 pages).
OBP Medical—ER-SPEC Brochure published Feb. 4, 2013 (2 pages).
OBP Medical—ER-SPEC Brochure, Light Source Now 10× Brighter published Jan. 23, 2013 (1 page).
Redefining illumination, Eikon LT Adapt SE For optimal precision and protection (2019), Stryker, www.stryker.com/surgical (3 pages).
The US Publications (# 1, 2) and WO references were cited in the Supplementary European Search Report dated Oct. 6, 2021 issued in European Application No. 19757432.0 , a copy of which is enclosed.

* cited by examiner

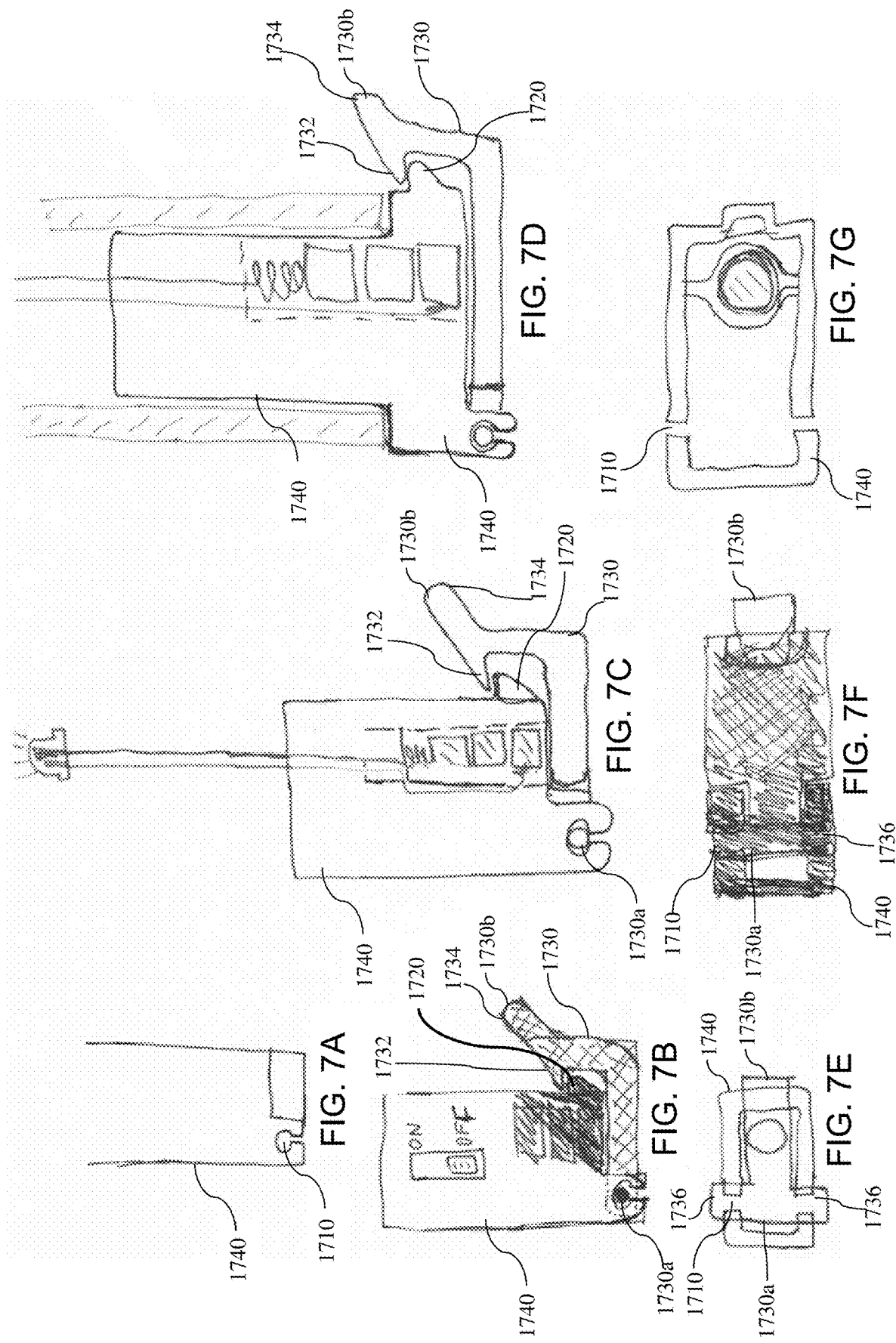

Top assembly is snapped into yoke.

Top assembly snaps into bottom assembly.

MEDICAL DEVICES WITH BATTERY REMOVAL

CROSS-REFERENCE TO RELATED APPLICATIONS

This application is a continuation application of application Ser. No. 16/402,580, which is a continuation application of application Ser. No. 16/105,153 filed Aug. 20, 2018, now issued as U.S. Pat. No. 10,278,572, and claiming benefit of provisional patent application Nos. 62/574,412 filed on Oct. 19, 2017, 62/574,969 filed on Oct. 20, 2019 and 62/649,190 filed on Mar. 28, 2018, the entire disclosures of which are incorporated herein by reference.

INTRODUCTION

The present invention relates to medical devices, such as speculums, retractors and suction devices, typically used for examination of a patient or during surgery. Conventional medical devices, including specula, may use an illumination means for illuminating the subject area for examination. For example, U.S. patent application Ser. Nos. 13/241,136 and 14/316,787 describe specula that include an illumination assembly for illuminating the subject area. These applications are incorporated herein by reference. Illumination assemblies or means typically use a light, such as an LED, and one or more power sources, such as batteries. For example, button batteries are used in the illumination assemblies described in the '136 and '787 applications.

After a disposable speculum is used on a patient, the speculum is disposed as biohazardous waste in accordance with medical waste disposal requirements. Biomedical waste is often incinerated by an appropriate entity. However, batteries usually contain metals, such as mercury, cadmium, zinc, nickel, chromium, lead and others. As a result, when batteries are incinerated along with the biomedical waste, heavy metals may contaminate the ash released by the incinerator, thus polluting the air. Moreover, metals in the batteries can leach out of landfills and pollute water sources. Therefore, proper disposal and recycling of batteries from used specula, without contaminating the batteries with biohazardous materials, is desired.

SUMMARY OF THE INVENTION

It is an objective of the present invention to provide a battery removal mechanism which allows for easy removal of batteries without risking contamination of the batteries with biohazardous materials.

In accordance with the present invention, a battery-powered medical device comprising: an outer housing having an opening formed therein, at least one power source housed within the outer housing, the outer housing being configured to at least partially enclose the at least one power source so as to prevent contamination of the at least one power source with biohazardous materials, and the at least one power source being removable from the outer housing via the opening, a cover configured to cover the opening in the outer housing and to retain the at least one power source within the outer housing, and an actuator provided within the outer housing that directly engages with a portion of the at least one power source when the cover covers the opening in the outer housing, wherein the cover is configured to be operated to expose the opening in the outer housing, and when the cover is operated to expose the opening, the actuator is configured to pull the at least one power source from the outer housing and the outer housing is configured to release the at least one power source via the opening without requiring physical contact between the user and the at least one power source, and wherein the outer housing comprises a handle and an operative portion coupled to the handle.

In certain embodiments, the actuator loops around a portion of the at least one power source. The actuator may be a band that loops around the power source. In some embodiments, the medical device is one of a retractor and a suction device.

In certain embodiments, the medical device further comprises an illumination assembly including at least one light source, and the at least one power source is configured to power the at least one light source. In some embodiments, the at least one light source is provided on the operative portion and the at least one power source is housed in the handle.

BRIEF DESCRIPTION OF THE DRAWINGS

The above and other features and aspects of the present invention will become more apparent upon reading the following detailed description in conjunction with the accompanying drawings, in which:

FIGS. 7A-7G show a portion of a medical device with a sixth embodiment of an illumination assembly of the present invention that allows for battery removal;

DETAILED DESCRIPTION

The present invention provides a medical device, such as a speculum, which includes an illumination assembly or the like with batteries, and in which the batteries can be easily removed by the doctor and recycled after the medical device is used on a patient. In particular, the medical device of the present invention enables a doctor to remove the batteries, while wearing gloves, without having the batteries come into contact with the doctor's gloves or other parts of the medical device.

Examples of illumination assemblies and specula with illumination assemblies are described in U.S. Pat. No. 9,307,897 and application Ser. No. 14/316,787 (US Pub. No. 2014/0309499) and Ser. No. 14/748,435 (US Pub. No. 2015/0289757), all of which are incorporated herein by reference. An illumination assembly of a cordless disposable speculum uses batteries, and it is preferable to separately dispose of or recycle these batteries. Conventional illumination assemblies do not provide for safe removal of the batteries from the speculum. As shown in FIGS. 1-14 and described below, the present invention contemplates several embodiments of battery removal mechanisms, which can be used in illuminated specula.

Figure 1:
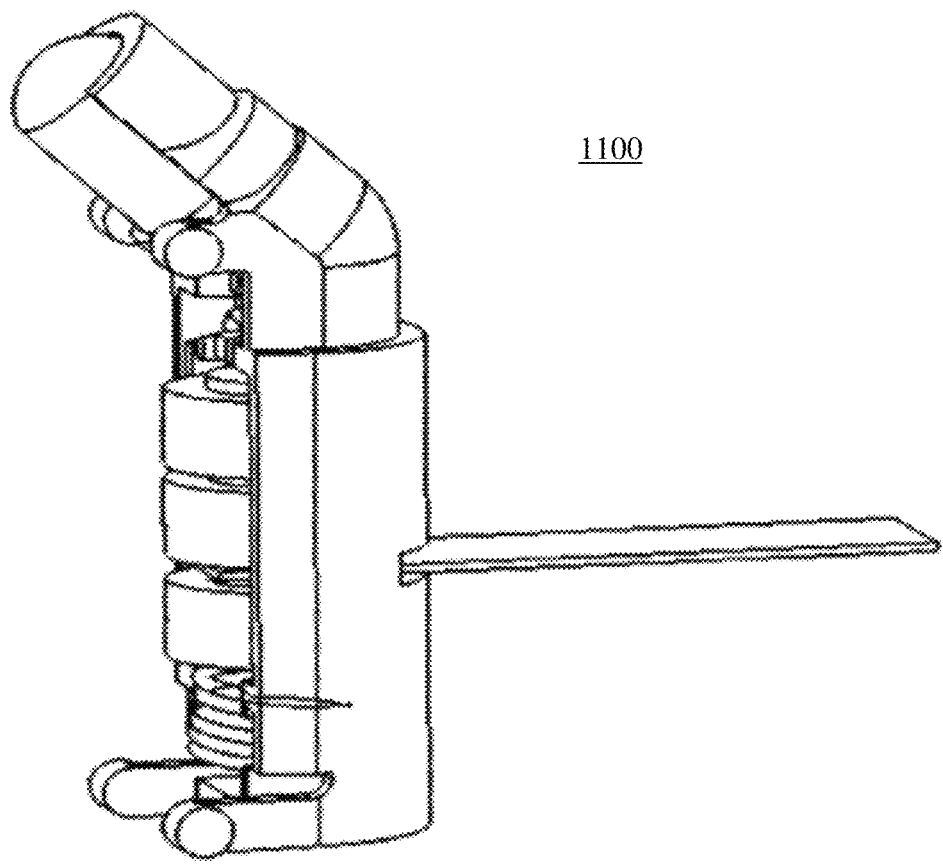
FIG. 1 shows a conventional illumination assembly for use with a disposable speculum.

In accordance with various embodiments of the present invention as set forth herein, an illumination assembly is defined by a structure (e.g., a housing or a casing) that retains at least a light source and a power supply. The illumination assembly in some instances may further contain one or more conducting/non-conducting circuit elements, one or more energization/de-energization switch elements, engagement/retention elements, etc. FIG. 1 shows an exemplary prior art illumination assembly. Further structural and operational details regarding these types of illumination assemblies are described in at least U.S. patent application Ser. No. 14/316,787 (US Pub. No. 2014/0309499) and Ser. No. 15/178,744 (US Pub. No. 2016/0310121), both of which are incorporated herein by reference in their entireties.

As shown in FIG. 1, the housing that defines the illumination assembly is a semi-enclosed (or partially enclosing) structure having at least one open side allowing access to or removal of its constituents. For example, the illumination assembly is configured to fully retain and securely hold the batteries and the contained light source upon placement of the illumination assembly onto a surface of a blade. Typically, the surface upon which the illumination assembly is placed (e.g., the speculum blade) provides the final, missing support for a full and complete retention.

As further shown in FIG. 1, the illumination assembly is configured to attach to a speculum blade via suitable engagement means (e.g., clips, adhesives, slots and tabs, etc.). The position of attachment of the illumination assembly along the blade varies from anywhere between a distal end of the blade and a proximal end of the blade, or within or extending along a curved portion (transition into handle portion) of the blade. In some prior art devices, the illumination assembly is contained entirely within the handle portion of the speculum and the light is directed to a desired area, e.g., the distal end of the speculum blade, via use of light guiding means such as a light pipe. In other prior art devices, at least of a portion of the illumination assembly is external to the device or positioned on an exterior surface thereof, e.g., on the exterior surface of the speculum blade.

The various embodiments of the present invention incorporate a similar illumination assembly but are not necessarily limited to use of the illumination assembly as shown in FIG. 1. In particular, the embodiments of the present invention as described herein, as well as their respective variants, are compatible with illuminating means of any size, shape or structure. Furthermore, although the embodiments described below are used in a speculum, it is also contemplated that the embodiments of the present invention are applicable to any medical or surgical device in which one or more of the entire medical or surgical device, the illuminating means, or the batteries are configured to be discarded after use.

Referring now to an exemplary embodiment of the present invention, a speculum apparatus having at least one blade and at least one an illumination assembly is provided, the illumination assembly being attached to the blade or handle and further having a bottomless battery compartment. The phrase "bottomless battery compartment" as used herein refers to a compartment within an illumination assembly for retaining one or more batteries in which the compartment does not completely permanently enclose the retained batteries. It is understood that the embodiments described below may be adapted for use with other medical and surgical devices, including but not limited to laryngoscopes, anoscopes, suction devices, electrocautery devices, and any other medical or surgical devices which use portable power sources, such as batteries or power packs.

Figure 2A:
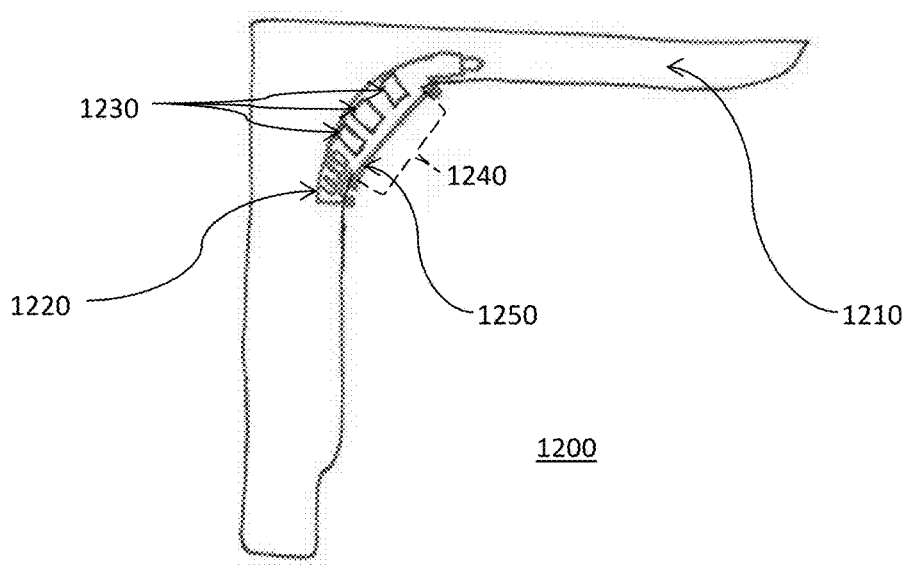
FIGS. 2A-2C show a medical device with a first embodiment of an illumination assembly of the present invention that allows for battery removal.

As shown in FIG. 2A, a speculum apparatus 1200 comprises a blade 1210, a handle, and an illumination assembly 1220 attached to the blade 1210. Only the lower member of the speculum is shown in the figures. In this embodiment, the illumination assembly 1220 includes a bottomless battery compartment that retains one or more batteries 1230. As described herein, the bottomless battery compartment does not provide any retaining support for the batteries along at least one of its sides, e.g., the bottom side of the compartment that comes in contact with the surface of the blade 1210.

In one version, the illumination assembly 1220 is a self-contained and standalone illumination assembly in which all of the batteries are at least loosely retained within the battery compartment by a small force (e.g., adhesive, spring, electromagnetic, etc.). In this version, a small outside force (e.g., shake, turbulence, push, jerk, etc.) applied to the illumination assembly or the apparatus causes the batteries to break loose via the open side of the battery compartment. In another version, the illumination assembly 1220 firmly retains the batteries within the battery compartment and requires a force exceeding a certain threshold to cause the batteries to break loose via the open side of the battery compartment.

In accordance with this embodiment, the blade 1210 comprises an opening 1240 that is aligned with the attachment position of the illumination assembly 1220. The opening 1240 of the blade 1210 is typically defined by a size or a hole that is sufficiently large to allow at least the batteries 1230 contained in the battery compartment to pass through and to be disposed. In one version, the opening 1240 may permit the entire illumination assembly to pass through and be disposed.

Figure 2B:
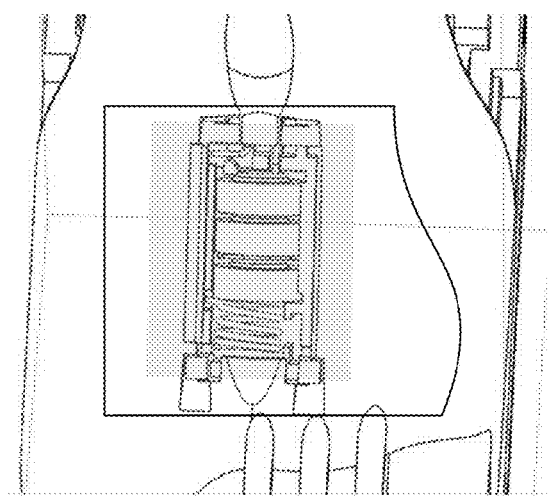

In accordance with this embodiment, the blade 1210 further comprises a cover 1250. The cover 1250 is typically provided on the external surface of the blade and covers the opening 1240. As shown in FIG. 2B, during a normal use of the apparatus 1200, the opening 1240 is sealed by the cover 1250. The cover 1250 in this state may be referred to herein as the "closed" position.

Figure 2C:
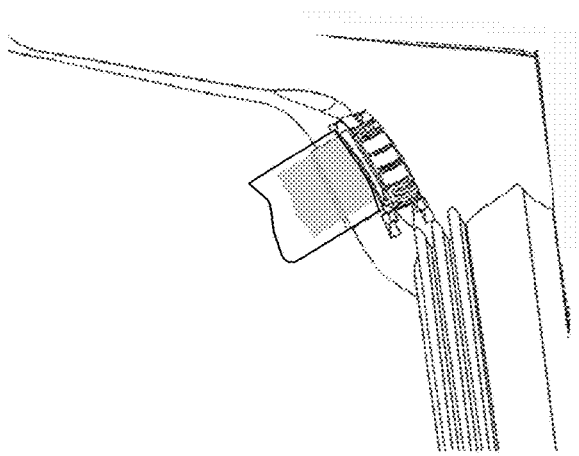

In one version, the cover 1250 is provided via an adhesive that allows the cover 1250 to be peeled off when disposal of the batteries is desired. For example, the cover 1250 is a sticker that is placed over the opening 1240 to secure the batteries 1230 against its surface. The sticker may be coated so that the batteries 1230 do not stick thereto but the sticker can be adhesively secured to the blade 1210. In another version, the cover 1250 is made of plastic material (e.g., same or similar substance as the blade). The plastic cover may be attached to the blade 1210 via adhesives, hinges, latches, clips, rails, screws, snaps or using other suitable techniques. The plastic cover may be articulated from the closed position to an "open" position by, for example, pressing onto the plastic cover, sliding the plastic cover, peeling the plastic cover, turning or rotating the plastic cover, etc. In some versions, a button may be used for releasing the cover when pressed. In a further version, the cover 1250 is formed as part of the blade 1210 itself. For example, the cover 1250 is a hinged door that opens/closes the opening 1240 or a slide door that exposes the opening 1240 for battery disposal. FIG. 2C shows an example of the cover 1250 in its "open" position.

As variations to one or more of the versions of this embodiment, the illumination assembly 1220, the opening 1240 and the cover 1250 may be positioned at the distal (front) end of the blade 1210, the center of the blade 1210, the proximal (rear) end of the blade 1210, or within the handle, or extends along two or more of these portions of the blade. Regardless of position, the operation of the illumination assembly with respect to the opening and the cover remains the same or substantially similar.

In accordance with this embodiment of the present invention, once the cover 1250 is either removed, peeled, or otherwise in the open position, the user can apply a force, such as shaking, pressing or bumping the apparatus, to "pop" the batteries 1230 out from their retained position. Upon such force, the batteries 1230 and/or the illumination assembly 1220 can be detached from the blade 1210 or the handle and can be disposed separately and safely from the rest of the apparatus 1200. In certain versions, no force is necessary to remove the battery(ies) and, in such versions, the batteries fall out when the cover 1250 is removed, peeled or otherwise in the open position. In yet other versions, a ribbon or the like may be passed behind the batteries and when the cover is removed, the ribbon can be pulled to dislodge and release the batteries.

Another embodiment of the present invention is provided with reference to FIGS. 3A-3D. In this embodiment, a speculum apparatus 1300 includes a blade 1310, an illumination assembly 1320 with one or more batteries 1330, an opening 1340 and a battery compartment 1350 for holding the one or more batteries. Again, only the lower member of the speculum is shown for ease of understanding. The structure and operation of the apparatus and the illumination assembly are the same as those described in reference to FIG. 2A, and thus, further description thereof will be omitted. It is understood that although FIGS. 3A-3D show the illumination assembly 1320 being disposed in the proximal end of the blade or in the area that joins the blade to the handle, in other embodiments, the illumination assembly may be provided in other areas of the blade, e.g., closer to the distal end, or in the handle portion of the apparatus in combination with a light guide or a similar device.

In accordance with this embodiment, the battery compartment 1350 houses the one or more batteries used in the illumination assembly and is inserted into the opening 1340 in the apparatus 1300. The battery compartment 1350 includes an opening 1350a at one end which allows the batteries 1330 to be electrically coupled with a light source of the illumination assembly when the battery compartment 1350 is in a closed state, and allows for removal of the batteries when the battery compartment 1350 is in an open state. In the closed state, the battery compartment 1350 acts as a cover for the opening wherein the outer wall of the battery compartment 1350 is coextensive with the walls of the blade and/or handle.

Figure 3A:
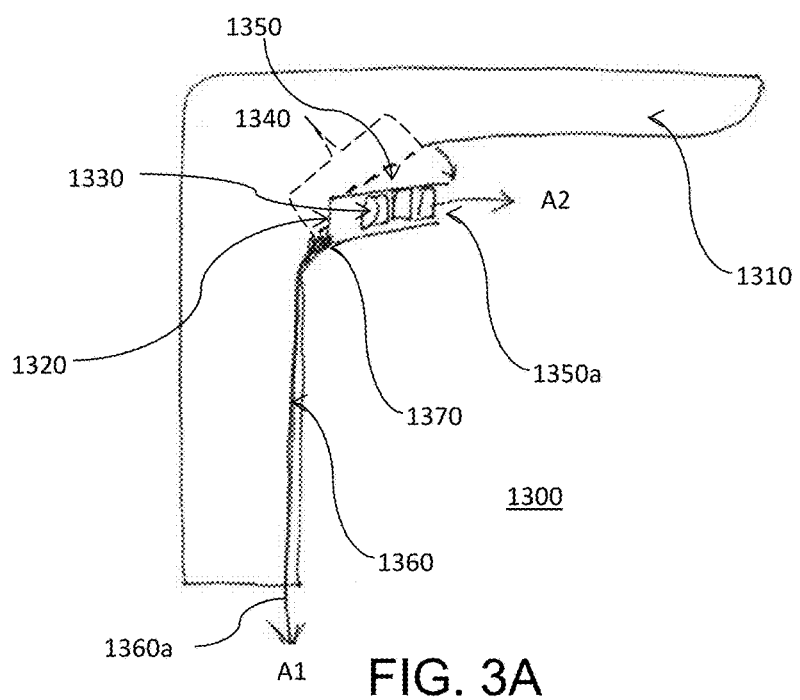
FIGS. 3A-3D show a medical device with a second embodiment of an illumination assembly of the present invention that allows for battery removal.
Figure 3B:
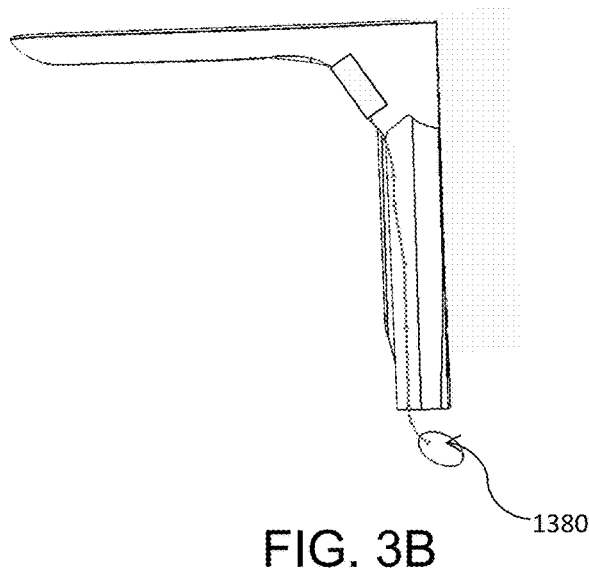
Figure 3C:
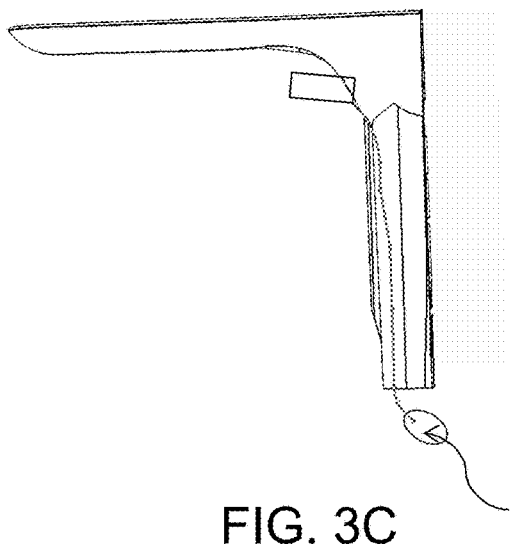

As shown in FIGS. 3A-3C, the battery compartment 1350 is articulated by operating a release mechanism that includes a release tab 1360 that can be moved from a first position in which the release tab 1360 holds the battery compartment 1350 in the closed state and a second position in which the release tab 1360 allows the battery compartment 1350 to drop down into an open state. In this illustrative embodiment, the release tab 1360 is engaged with the battery compartment 1350 at point 1370, but in other embodiments, the release tab 1360 may be engaged with the battery compartment 1350 at other points or other types of release mechanisms to move the battery compartment from the first position to the second position may be used.

As shown in FIGS. 3B and 3C, the release tab 1360 is coupled to a pull-down member 1380 via a connection line 1360a, which extends down through the handle portion of the apparatus. The pull-down member 1380 may be inserted into or engaged with the distal end of the handle so as to form a cap or the like which can be easily removed from the handle by the user and pulled down so as to move the release tab 1360 into the open state.

In operation, the user pulls on the pull-down member 1380 in the direction indicated by the arrow A1, causing the release tab 1360 to move from the first position to the second position so as to cause the battery compartment 1350 to articulate from its closed position to its open position and to cause the batteries 1330 to be disposed in the direction indicated by the arrow A2 through the opening 1350a in the battery compartment. In one version, the release tab 1360 opens a cover 1350 on the blade and only the batteries are disposed through the opening 1350a in the battery compartment. In another variation, the battery compartment may be replaced with an illumination assembly compartment holding the entire illumination assembly so that the entire illumination assembly can be disposed via the opening 1340 when the illumination assembly compartment is in the open state. In another variation, the pull-down member 1380 is connected directly to the battery compartment 1350 or the illumination assembly compartment, and when the pull-down member 1380 is pulled, the battery compartment or the illumination assembly compartment is disengaged from the closed state and the batteries or the whole illumination assembly is disposed.

FIG. 3B shows an example of a pull-down member prior to activation and FIG. 3C shows an example of the pull-down member after activation in which the battery compartment is pushed through the opening of the blade. As shown, the pull-down member may be freely hanging from the handle in some embodiments, while in other embodiments, the pull-down member may be engaged with the distal end of the cap to form an end cap or the like that is removable from the handle. In yet other embodiments, the pull-down member may be replaced by another activation mechanism, such as a switch or a pull-tab provided on the handle of the apparatus. In yet further embodiments, the activation mechanism may be disposed within the interior of the handle and is engaged or otherwise activated by placing a tool or a finger inside the handle from its open end. For example, a switch, a button, a pull-tab, a pull-down member or any other suitable mechanism may be provided on the interior of the handle or on the interior wall of the handle. In such embodiments, the activation mechanism cannot be accidentally triggered.

In the embodiment described above with respect to FIGS. 2A-2C, the battery removal mechanism uses a battery compartment or an illumination assembly compartment which is articulated between the closed position and the open position so as to release the batteries and/or the illumination assembly from the apparatus for disposal. In other embodiments, the battery removal mechanism may use a cover for covering the opening 1340 and for articulating between the first position in which the cover is closed and the batteries and/or illumination assembly are retained in the apparatus and the second position in which the cover is open and the batteries and/or illumination assembly can be removed from the apparatus through the opening 1340 and disposed. The same or substantially similar release mechanism is used for causing the cover to articulate between the first and second positions. In these embodiments, the batteries may be housed within a separately formed battery compartment so that when the cover is opened, the entire battery compartment with the batteries is removed. In other variations, the whole illumination assembly is housed within an illumination assembly compartment so that when the cover is opened, the illumination assembly compartment is removed, thus disposing of the entire illumination assembly. In yet other variations, the batteries are held in a partially open battery or illumination assembly compartment or case, which has an opening coextensive with the cover, so that when the cover is opened, the batteries drop down from the partially open compartment and can be disposed.

Figure 3D:
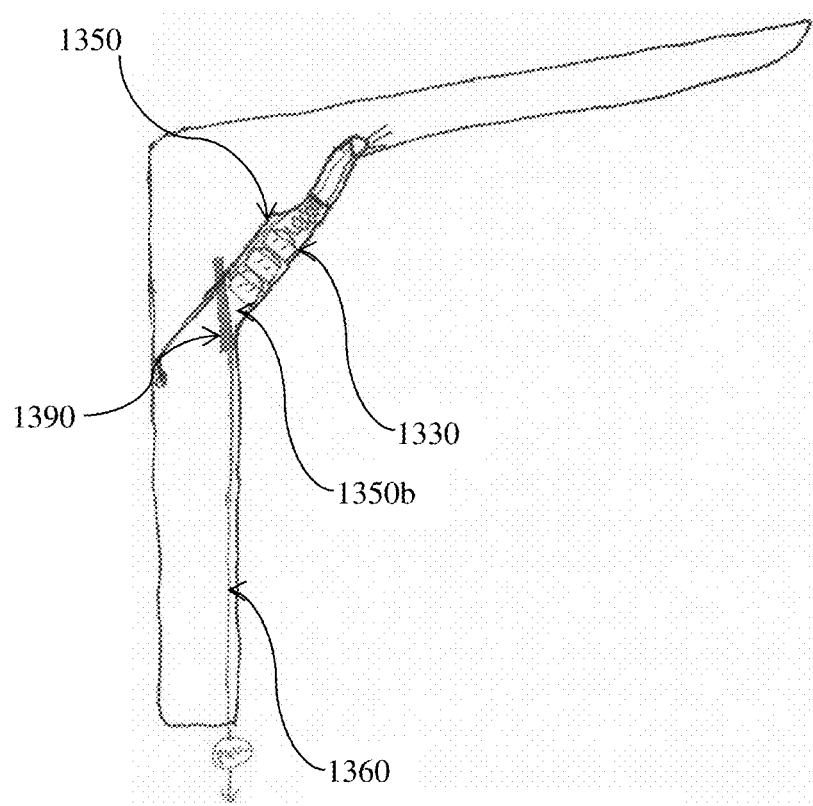

A further variation of this embodiment is shown in FIG. 3D. In this version, the battery compartment 1350 includes one or more batteries 1330 and an opening 1350*b* that opens into the handle portion of the apparatus. Specifically, in this version, the battery compartment 1350 is further configured with a closing tab (or a "door") 1390 that holds the batteries 1330 within the battery compartment 1350, when the closing tab 1390 is in a closed state. As shown in FIG. 3D, the batteries 1330 rest on the closing tab 1390 in the closed state. In the illustrated example of FIG. 3D, the batteries are disposed in the area that connects the blade to the handle portion on an angle relative to the blade and to the handle portion. However, in other variations, the batteries may be disposed in other areas of the apparatus, such as within the handle or in the blade area and the orientation of the batteries may be varied depending on the construction of the illumination assembly. For example, the battery compartment may be provided in the handle portion in a substantially vertical orientation so that the batteries are supported by the closing tab 390 in the closed state.

In FIG. 3D, for disposal of the batteries, the closing tab 1390 is actuated from its closed state to an open state by pulling on the release tab 1360. For example, the user can pull on the release tab 1360 that hangs loose through the handle portion causing the closing tab 1390 to detach from the battery compartment 1350, allowing the batteries 1330 to drop down through the handle portion of the speculum. In one version, the entire closing tab 1390 is detached. In this version, the closing tab, once detached, is also dropped through the handle portion. In another version, the detachment of the closing tab 1390 is only partial. In this version, pulling of the release tab 1360 partially breaks the attachment of the closing tab 1390 to the battery compartment 1350 and allows the closing tab 1390 to remain partially attached to the battery compartment 1350 (e.g., swinging via a hinge) to release the batteries via the handle portion. In yet other versions, the closing tab may be hingedly, rotatably or slidably connected to the battery compartment 1350 or to the handle portion and may be held in the closed state until the release tab 1360 is pulled. In certain variations, a spring member may force the closing tab 1390 into the closed state, while in other variations, the closing tab 1390 may be mechanically coupled with the battery compartment 1350. Pulling of the release tab 1360 in these versions would cause the closing tab 1390 to rotate or to slide relative to the opening in the battery compartment into the open state so that the batteries can be dropped into and through the handle portion.

Figure 4:
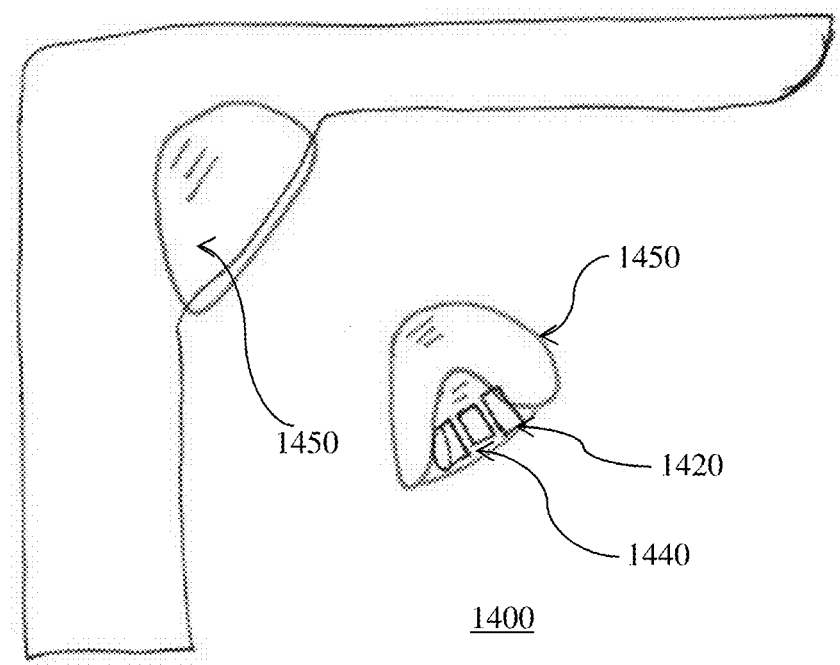
FIG. 4 shows a medical device with a third embodiment of a portion of an illumination assembly of the present invention that allows for battery removal.

A further embodiment of the present invention is shown in FIG. 4. In this embodiment, a speculum apparatus 1400, similar to those described in reference to FIG. 2A, includes similar components such as the blade, the illumination assembly with one or more batteries, an opening formed in the blade or handle, and a cover for the opening. In this embodiment, the illumination assembly 1420 may include a bottomless battery compartment with an opening that corresponds to the opening in the blade or handle. Alternatively, the illumination assembly 1420 may be a self-contained illumination assembly with a housing that partially houses the illumination assembly and in which the one or more batteries are at least loosely retained by the housing by a small force. In such variation, an opening in the housing for the illumination assembly corresponds at least in part with the opening in the blade or handle.

As shown in FIG. 4, the opening in the blade or handle is covered by the cover 1450 which may be formed from a plastic, polymer or rubber material. The cover 1450 is releasably attachable to the handle or blade or the apparatus. Any suitable fastening or attachment mechanism may be used for releasably attaching the cover to the handle or blade of the apparatus, including but not limited to providing protrusions and corresponding recesses or slots on the cover and handle or blade, using an adhesive to attach the cover to the handle or blade, or any suitable fastener. The cover 1450 may be completely removable from the handle or blade of the apparatus or in certain embodiments, the cover 1450 may be hingedly connected to the handle or blade so as to open and close relative to the blade or handle. In yet other embodiments, the cover 1450 may be elastic and squeezable, so that the cover is fitted into the opening in the handle or blade of the apparatus and can be removed by squeezing the cover on the sides to detach it from the opening.

During operation of the apparatus, the cover 1450 covers at least the one or more batteries and retains them in the illumination assembly 1420. After the operation is completed and before disposing the apparatus, the cover 1450 is removed to expose the batteries, and the batteries can then be removed by a small outside force such as a shake, or a jerk, applied to the apparatus. In certain embodiments, the cover 1450 forms an elastic and squeezable layer around a portion of the batteries so that the cover 1450 is depressible or squeezable by the user for releasing the contained batteries. Specifically, pressing on the sides of the squeezable cover 1450 forces the batteries to be released through the opening 1440 and to be removed simultaneously with the cover 1450. The user can then dispose the batteries while holding the cover over the recycling container for the batteries. In another variation, the cover has to be articulated by sliding, rotating or the like so as to cause the batteries to be released and removed together with the cover.

In another exemplary embodiment of the present invention, a speculum apparatus, is provided in which one or more batteries for powering a light source are provided within the handle portion thereof. It is understood that this embodiment may also be applied to another medical device apparatus, such as a retractor, laryngoscope, anoscope, suction device, or the like. In accordance with this embodiment, the illumination assembly is structured such that the batteries for powering the light source are retained in the handle portion and the light source is positioned along the blade or some other component of the apparatus where illumination is needed. The batteries are connected to the light source using wires. In some versions, the illumination assembly is structured such that the batteries and the light source are both retained in the handle portion and the light is directed to the area where illumination is needed, e.g., the distal end of the blade, using a light directing means (e.g., a light pipe, prism, mirrors, etc.).

Figure 5:
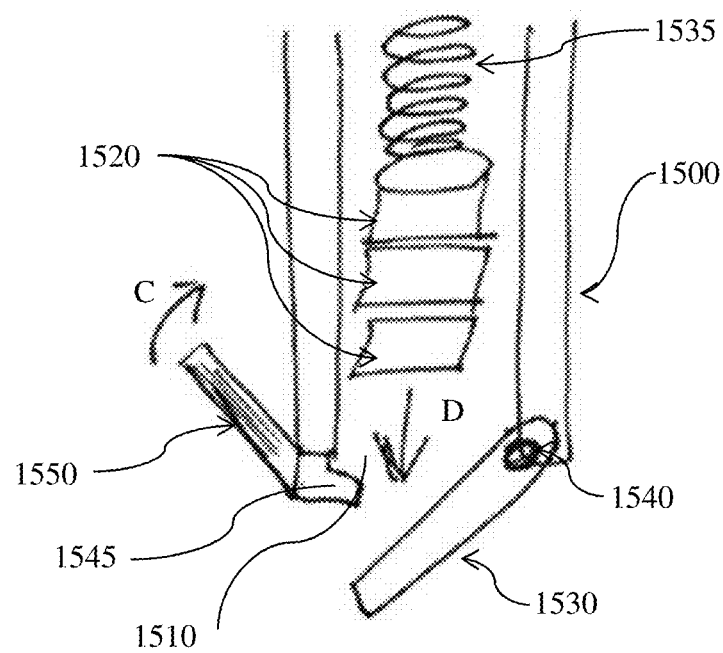
FIG. 5 shows a portion of a medical device with a fourth embodiment of a portion of an illumination assembly of the present invention that allows for battery removal.

Referring now to the battery removal aspect, the apparatus as shown in FIG. 5 includes a handle portion 1500 having an open-bottom receiving end 1510 for receiving and retaining one or more batteries 1520. In accordance with this embodiment, the open-bottom receiving end 1510 of the handle portion 1500 is covered by a platform 1530 that forms an end cap or end wall of the handle portion. The platform 1530 is hingedly (or rotatably) attached to the handle portion 1500 via a hinge 1540, and is locked in place by a tab 1545 and a release switch 1550. When the release switch 1550 is actuated in the direction indicated by the arrow C, the tab 1545 is moved away from a closed position and the platform 1530 drops down and rotates via the hinge 1540, which causes the batteries 1520 retained in the handle portion to be disposed in the direction indicated by arrow D. Although this illustrative embodiment uses a tab 1545 to hold the platform 1530 in a closed position and to release the platform 1530 into the open position, it is contemplated that other mechanisms may be used for retaining the platform 1530 in the closed state and for releasing the platform to allow it to drop down.

In this embodiment, it should be noted that the batteries 1520 are merely resting upon the platform 1530 when the platform is in its "closed" position and a biasing member, such as a spring, may be used to bias the batteries 1520 in a direction of the platform 1530. As shown in FIG. 5, the spring 1535 is provided above the batteries and pushes the batteries toward the platform 1530. As a result, when the release switch 1550 is actuated to open the platform 1530, the batteries are pushed out of the handle by the force of the spring 1535.

In one version, when the entire illumination assembly is positioned within the handle portion of the apparatus, all or a portion of the illumination assembly may be adhesively or mechanically attached to the handle portion. However, the batteries may be held by a bottomless battery compartment with an opening at the bottom covered by the platform 1530, or as shown in FIG. 5, the handle portion may form the bottomless battery compartment that houses the batteries. In either case, when the platform 1530 is opened, the batteries can drop down through the open-bottom receiving end 1510 of the handle portion.

In another version, the light source of the illumination assembly is attached to the blade portion or some other portion of the apparatus where illumination is needed, and the batteries are retained in the handle portion of the apparatus, either in a separate bottomless compartment or in the handle portion itself forming the bottomless battery compartment that houses the batteries. In this version, the batteries may be held in place within the handle portion or within the separate bottomless compartment using a biasing member, an adhesive or some other retention force, but application of an external force to the apparatus causes the batteries to drop out when the platform 1530 is opened. As a variation to this version, the apparatus may further comprise one or more buttons or a separate switch that causes the batteries to drop loose.

Figure 6A:
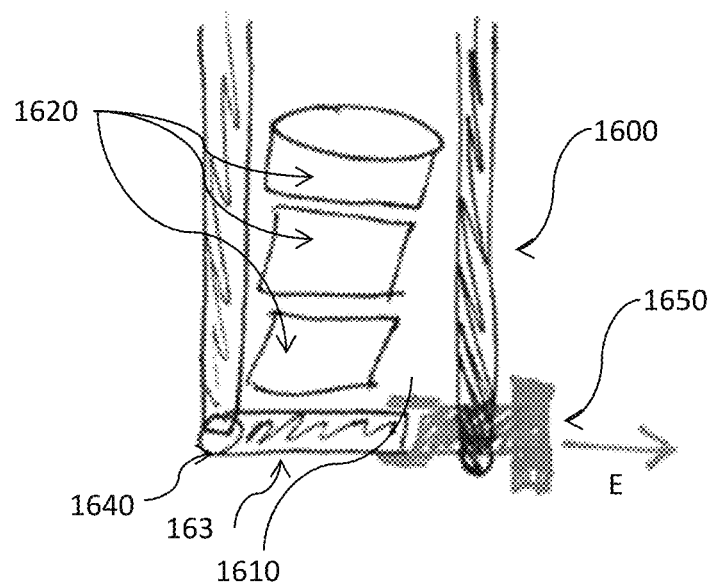
FIGS. 6A-6D show a medical device with a fifth embodiment of an illumination assembly of the present invention that allows for battery removal.
Figure 6B:
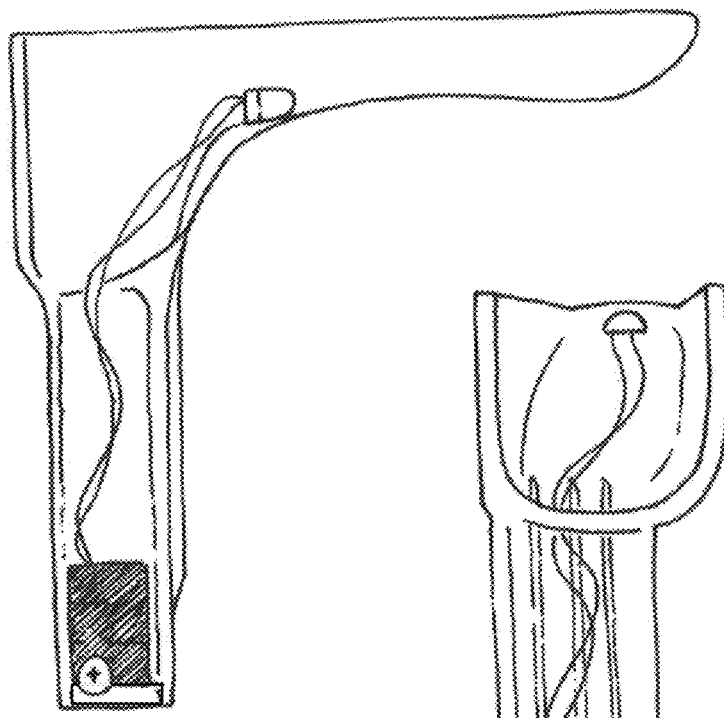
Figure 6C:
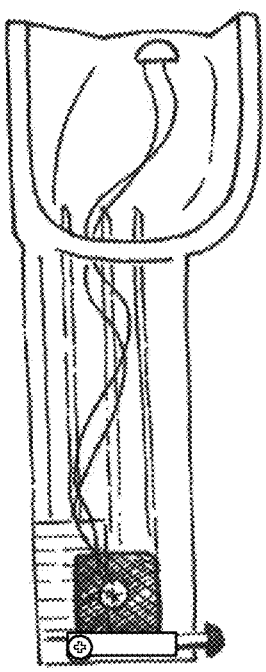

As a variation to this embodiment, the apparatus shown in FIG. 6A comprises similar components as the apparatus shown in FIG. 5, but further comprises a pull switch 1650 in place of the tab 1545 and the release switch 1550 as described with reference to FIG. 5. In one version, the handle portion 1600 includes one or more slots or holes near its open-bottom receiving end 1610 through which the pull switch 1650 passes. The pull switch 1650, in its "closed" (or inserted) position, attaches to or otherwise secures to the platform 1630. Although FIG. 6A shows the pull switch 1650 holding the platform 1630 at the top and bottom, in other variations, the pull switch 1650 may hold only the bottom of the platform 1630. In yet other variations, the pull switch 1650 may be inserted into a corresponding opening in the platform 1630 side edge so as to hold it in the closed position, as shown in FIG. 6C. Any other type of engagement between the pull switch 1650 and the platform 1630 may be used to releasably engage the pull switch 1650 with the platform 1630 in the closed state. Moreover, a biasing member, such as a spring member, may be used with the pull switch 1650 to bias the pull switch 1650 in the direction of the closed position. In this way, a predetermined pulling force on the pull switch 1650 would be needed in order to disengage the pull switch 1650 from the platform 1630 so as to prevent accidental opening of the platform 1630.

When the pull switch 1650 is articulated (in direction indicated by arrow E) to its "open" (or pulled) position, the pull switch 1650 separates from the platform 1630 and the platform 1630 drops down and rotates via the hinge 1640. The batteries are disposed in the handle portion in the same manner as discussed herein in reference to FIG. 5 above, and thus, separate discussion thereof is omitted. FIGS. 6B-6C show different perspective views of the apparatus as shown and described in FIG. 6A.

Figure 6D:
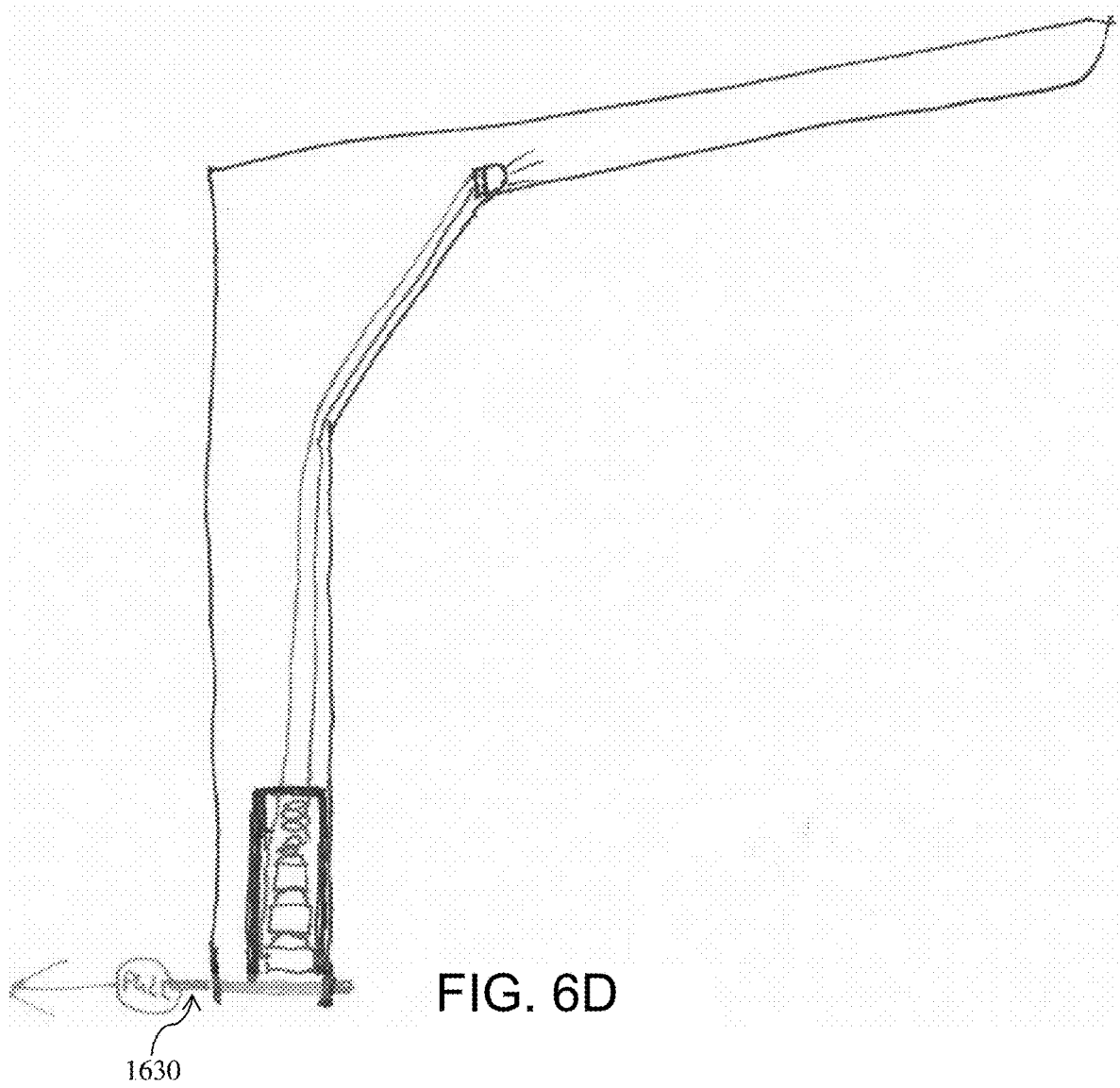

As a further variation of this embodiment, the entire platform 1630 may pass through slots formed in opposing walls of the handle portion. As shown in FIG. 6D, the platform 1630, having a length that traverses the entire width of the handle portion and provides a resting surface for the batteries, is provided in place of the platform-and-the-pull-switch combination shown in FIG. 6A. In this version, corresponding slots are provided in opposing walls of the lower end of the handle portion allowing the platform to be pulled in either direction. In an alternative configuration, the platform may be pulled only in one direction and may be prevented from being pulled in the other direction, e.g., by a flange or the like. Similar to the foregoing versions, once the platform 1630 is removed, the batteries drop through the open end of the handle portion.

As further variations to embodiments as described in reference to FIGS. 5 and 20, the platform may be articulated from its closed position to open position via different methods. For example, the release switch may be an external push button that releases the platform. For instance, a variation that includes a battery holding compartment with a pivotable platform is shown in FIGS. 7A-7G. As shown in FIGS. 7A-7C, a battery holding compartment 1740 is used for housing the batteries therein and for coupling the batteries, e.g., using wires, to the light source or to any other component of the apparatus that requires power supply. As shown in FIG. 7D, the battery compartment 1740 is inserted into an open end at the bottom of the handle portion of the apparatus. Although FIGS. 7A-7C show a separate battery holding compartment 1740 for housing the batteries and for releasing the batteries from the apparatus, in other embodiments, the handle portion may be configured to house the batteries directly therein and a similar pivotable platform mechanism may be used at the bottom of the handle portion as the one shown in FIGS. 7A-7C.

As shown in FIGS. 7A-7C, a bottom end of the battery holding compartment 1740 is provided with an opening 1710, which may be circular in cross section or any other suitable shape, and a mating portion 1720, which in this illustrative example is shown as a protrusion. As more clearly shown in FIG. 7B, a pivotable platform 1730 is provided, with the pivotable platform 1730 having a pivoting end 1730*a* and a mating end 1730*b*. The pivoting end 1730*a* pivotably engages with the opening 1710 formed on the bottom end of the battery holding compartment 1740. The mating end 1730*b* engages with the mating portion 1720 in a closed state so as to lock the pivotable platform 1730 relative to the battery holding compartment 1740. In the illustrative embodiments shown in FIGS. 7B-7D, the mating portion 1720 of the battery holding compartment 1740 is formed as a protrusion extending outwardly from a sidewall of the battery holding compartment 1740. In such embodiments, the mating end 1730*b* of the pivotable platform 1730 includes a locking tooth 1732 that mates with the mating portion 1720 so as to lock the pivotable portion 1730 in the closed state, and further includes an operating tab 1734 which can be operated by a user to release the mating between the locking tooth 1732 and the mating portion 1720. When the operating tab 1734 is actuated by a user (e.g., by pressing), the lock between the locking tooth 1732 of the pivotable platform 1730 and the mating portion 1720 is released and the pivotable platform 1730 may be pivoted into the open state relative to a pivot point at the pivot end 1730*a*. In other illustrative embodiments, the mating portion 1720 may be formed as a recess so that the locking tooth 1732 of the mating end 1730*b* is inserted into the mating portion 1720 recess in the closed state. Other configurations of the mating portion 1720 and the mating end 1730*b* may be used for providing a locking mechanism for locking the pivotable platform 1730 to the battery holding compartment 1740.

As further shown in FIG. 7C, the pivotable platform 1730 in its "closed" position provides a surface on which one or more batteries rest within the battery holding compartment 1740. The batteries are electrically connected to a distantly positioned light source via electrical wires extending through the handle portion. For disposal of the speculum and/or the batteries, the pivotable platform 1730 is released from engagement with the mating portion 1720 via an external force applied to the operating tab 1734 at the mating end 1730*b*. The pivotable platform 1730 then pivots via the pivoting end 1730*a* and permits the batteries to drop through the open bottom of the speculum handle portion. As shown in FIGS. 7C-7D, a spring or another type of biasing member may be provided at the top of the batteries so as to bias the batteries in the direction of the opening in the battery holding compartment, i.e., in the direction of the pivotable platform 1730.

In the embodiment described above and shown in FIGS. 7B-7D, the pivotable platform 1730 is configured together with a battery holding compartment 1740 as a standalone structure. In such version, as shown in FIG. 7D, the battery holding compartment is sized and/or shaped such that it is insertable (or fittable) into the hollow end of the handle portion. In this version, the mating portion is included on the battery compartment 1740. When the standalone structure is received a certain length within the hollow end of the handle portion, the user can actuate, by operating the operating tab 1734, the mating end 1730*b* of the pivotable platform 1730 to pivot the platform to its open position.

FIGS. 7E-7G show respective bottom views of the foregoing examples of FIGS. 7B-7D. As shown in FIGS. 7E and 7G, the battery holding compartment 1740 includes openings or recesses 1710 in opposing walls thereof at the lower end. In FIG. 7E, the pivotable platform 1730 includes a pair of legs or shafts 1736 projecting from the sides of the platform at or near the pivoting end 1730*a*. The legs 1736 are inserted into the corresponding openings or recesses 1710 in the walls of the battery holding compartment 1740. In the illustrative example shown, the openings or recesses 1710 have a smaller cross-section than the thickness of the legs 1736 at an initial point of insertion, with the cross-section increasing to accommodate the thickness of the legs. In this configuration, the legs 1736 of the platform 1730 snap into the openings or recesses 1710, and can be prevented from disengaging from the openings or recesses 1710. As shown in FIG. 7E, the body of the platform may be narrower than the opening in the battery holding compartment 1740 as long as the platform 1730 can retain the batteries within the battery holding compartment 1740. In other variations, the body of the platform 1730 is the same width or wider than the opening in the battery holding compartment 1740.

Figure 8A:
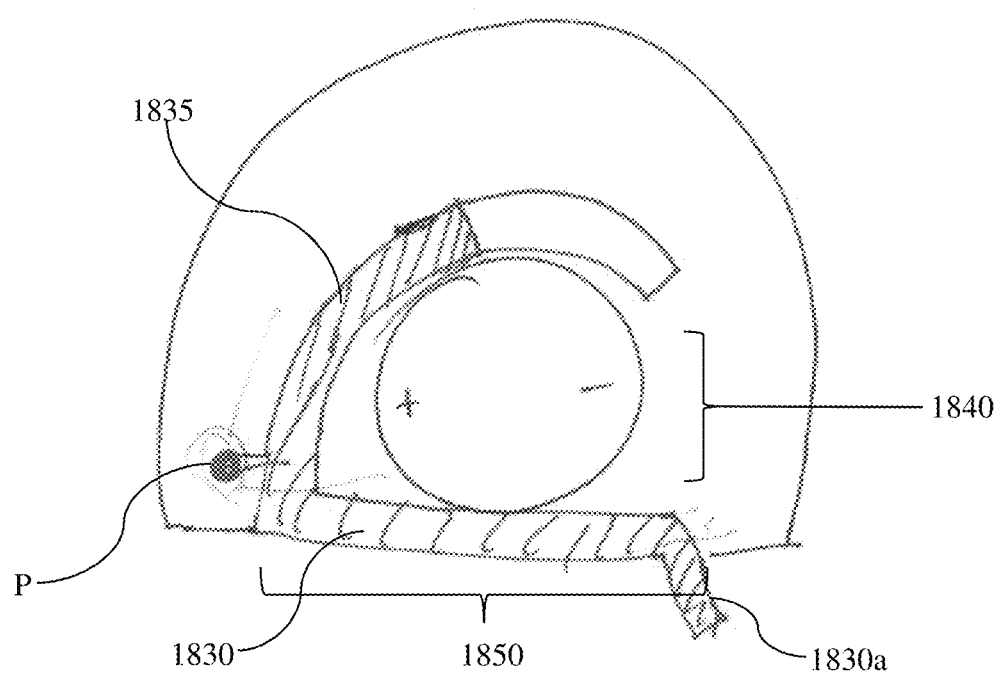
FIGS. 8A-8B show a portion of a medical device with a seventh embodiment of an illumination assembly portion of the present invention that allows for battery removal.
Figure 8B:
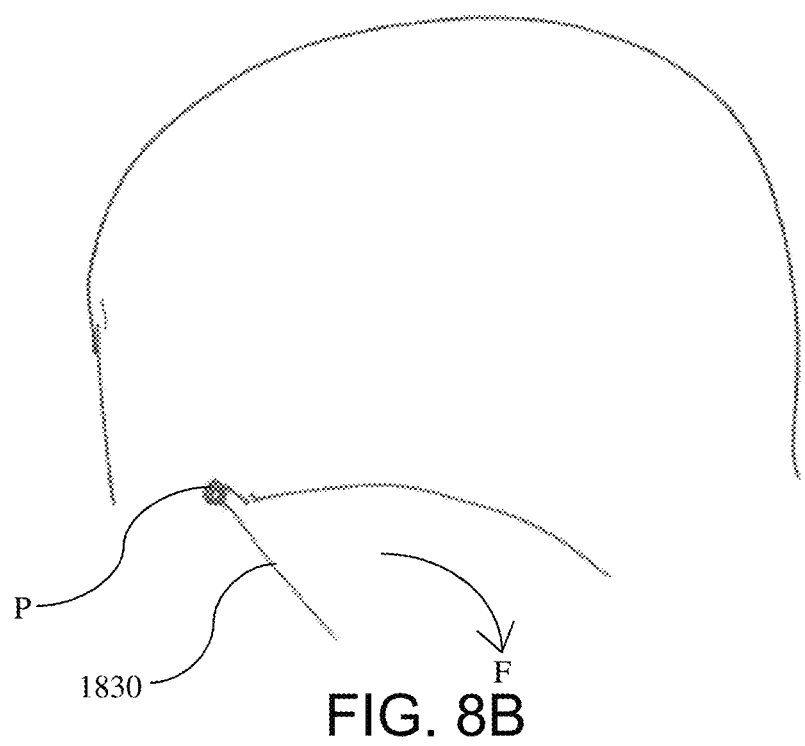

Another embodiment of a battery removal mechanism for removing and disposing batteries from a speculum or retractor apparatus is shown in FIGS. 8A-8B. FIGS. 8A-8B show a cross-sectional view looking axially down a handle portion having a battery ejection mechanism for removing batteries disposed within the handle portion through an opening 1850 formed in a sidewall of the handle portion. The ejection mechanism includes a door 1830 that covers the opening 1850 in the handle portion and includes with an ejection lever 1835 extending partially around the batteries housed within the handle portion. The door 1830 is pivotable around a pivot point P between a closed state, shown in FIG. 8A, and an open state shown in FIG. 8B. The door 1830 also includes an operation tab 1830*a* which can be operated (e.g., by pressing) by a user to open the door 1830 so as to move it from the closed state to the open state. When the door 1830 is opened, the ejection lever 1835, which moves together with the door 1830, pushes the batteries through the opening 1850 in the handle, thereby ejecting the batteries from the apparatus.

More specifically, as shown in FIG. 8A, the door 1830 is in its closed state. The door 1830 and the ejection lever 1835 are structured and/or shaped in a manner such that the one or more batteries can be released (or pulled) through an side opening 1840 formed between the door 1830 and the ejection lever 1835 using a small force or without using any force. In one version, the door 1830 and the ejection lever 1835 may be made of elastic material and the size of the side opening 1840 is smaller than the diameter of the retained batteries. In this version, a small force, such as a tap on the handle or a shake, would be required to release the batteries when the door 1830 is in the open state. In another version, the door 1830 and the ejection lever 1835 are made from plastic or polymer materials and the size of the side opening 1840 is the same or larger than the diameter of the batteries.

In this version, no force is needed to release the batteries when the door is in the open state.

When the operation tab 1830b on the door is operated by a user, the door 1830 and the ejection lever 1835 rotate around the pivot point P, and as they rotate, the side opening 1840 formed between the door and the ejection lever is exposed through the side opening 1850 in the handle portion, and the batteries are pulled/pushed forward and out the opening 1850 in the handle portion. As discussed above, the batteries may be released through the side opening 1840 with no or little force. FIG. 8B illustrates the batteries being released in the direction indicated by arrow "F." As a variation to the embodiment shown in FIGS. 8A and 8B, a column-shaped structure (hereinafter "structure") with a hollow center and sidewalls for retaining and partially enclosing one or more batteries may be provided in the handle portion. The structure may have a platform for supporting the one or more batteries thereon, with the platform being connected to the sidewalls so as to be movable together with the rest of the structure. The structure is sized to be insertable and pivotable through the opening 1850 in the handle portion of the apparatus relative to the pivot point P. The cross-section of the sidewalls of the structure is substantially the same or similar to that of the door and ejection lever shown in FIG. 8A. Similar to the door and the ejection lever shown in FIG. 8A, the structure includes a circumferential sidewall that covers the opening 1850 in the handle portion of the apparatus and extends around the one or more batteries but does not completely encircle the batteries. For example, the circumferential sidewall includes an opening that allows the retained batteries to be released therethrough when the structure is rotated from the closed state to the open state. The rotation of the structure about the pivot point and the release mechanism for the batteries in the structure are similar to those described with respect to FIGS. 8A and 8B.

Further variations to the embodiments described in reference to FIGS. 5-8 are also contemplated. For example, the release switch shown in FIG. 6A may be an external push button that releases the platform. As another example, the platform shown in FIG. 6D may include further components that can be pushed or pulled to assist in articulation of the platform to its open position.

Figure 9A:
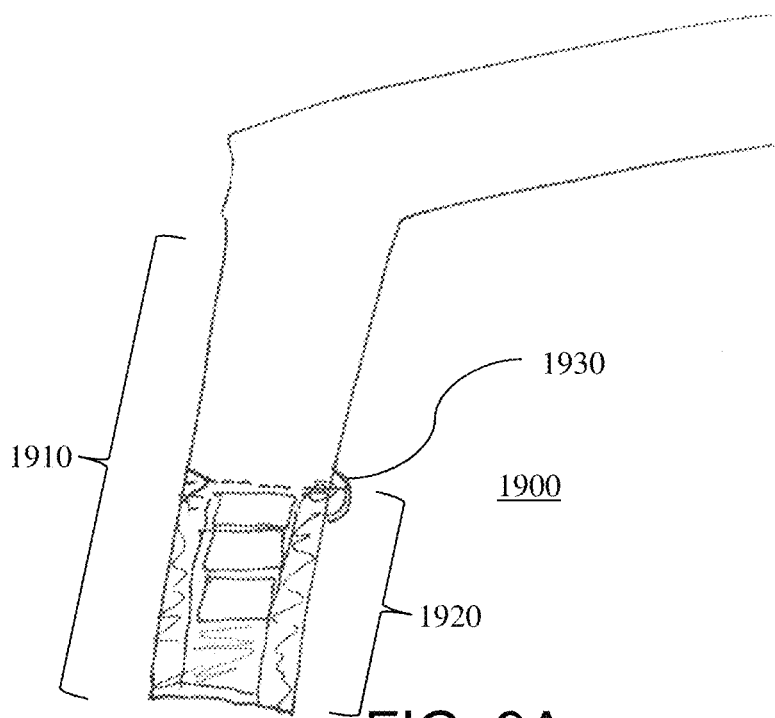
FIGS. 9A-9B show a portion of a medical device with an eighth embodiment of an illumination assembly portion of the present invention that allows for battery removal.
Figure 9B:
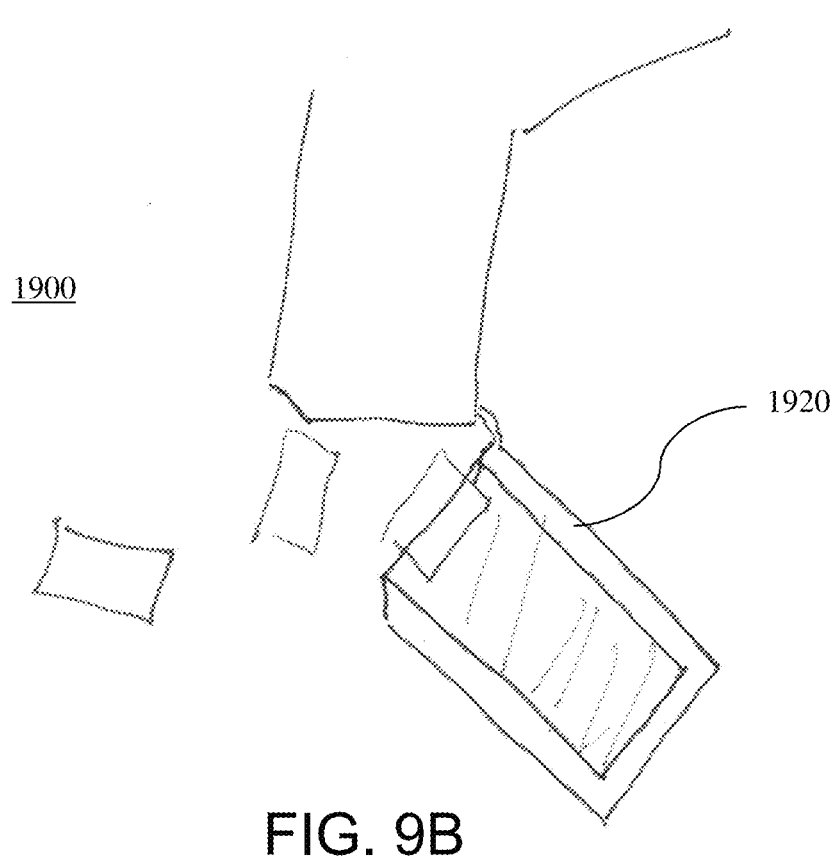

In yet another embodiment of the present invention, the handle portion of the apparatus is configured such that at least a portion thereof is breakable or detachable from the rest of the handle portion. As shown in FIG. 9A, the apparatus 1900 includes a handle portion 1910 in which a lower end portion 1920 is breakable or detachable from the remaining portion of the handle portion 1910. In accordance with this embodiment of the present invention, one or more batteries are retained within the lower end portion 1920 that is breakable or detachable from the rest of the handle portion 1910. In one embodiment, the breakable lower end portion 1920 completely detaches from the rest of the handle portion 1910. In another version, a hinge 1930 is provided between the breakable lower end portion 1920 and the rest of the handle portion 1910 such that when the breakable lower end portion 1920 is articulated to be "broken off" or detached from the handle portion 1910, the breakable lower end portion 1920 hinges via the hinge 1930 and the one or more batteries retained therein are released and can be disposed. FIG. 9B illustrates disposal of the batteries when the breakable lower end portion 1920 is separated from the rest of the handle portion of the apparatus and hinges via the hinge 1930. Actuation of the breakable lower end portion 1920 as described herein may be enabled using a variety of different methods such as manual force (pressing, twisting, pulling, etc.), a pull switch, a push button, or other similar techniques. The embodiments as described herein are intended to present a concept of separate disposal for batteries used in a medical device. In certain embodiments, a platform placed at the bottom end of the handle portion of the speculum apparatus or another medical device is opened in one of many different ways to allow the batteries to be disposed separately and quickly. In certain other embodiments, the blade or handle of the speculum or another apparatus includes an opening through which the batteries held in a bottomless battery compartment of an illumination assembly are disposed separately and quickly. In certain other embodiments, portions of the medical device that retains the batteries are detached completely or partially from the medical device itself. Separate disposal of batteries solves the problems of hazardous contamination and/or pollution of the environment. Furthermore, since the batteries are removed from the speculum at the time of disposal, users need not worry about throwing out lit up speculums in the trash.

FIGS. 10A-14G show another embodiment of a speculum 2000 which includes a battery removal mechanism which uses a battery compartment 2060 (also referred to as a "battery sled") provided in a handle 2034 of the speculum 2000. The battery compartment 2060 holds batteries 2074 within the handle 2034 in a retained state, which is the operating state of the speculum, and allowing the batteries 2074 to be released and disposed through an opening in a bottom of the handle in an ejected state.

Figure 10A:
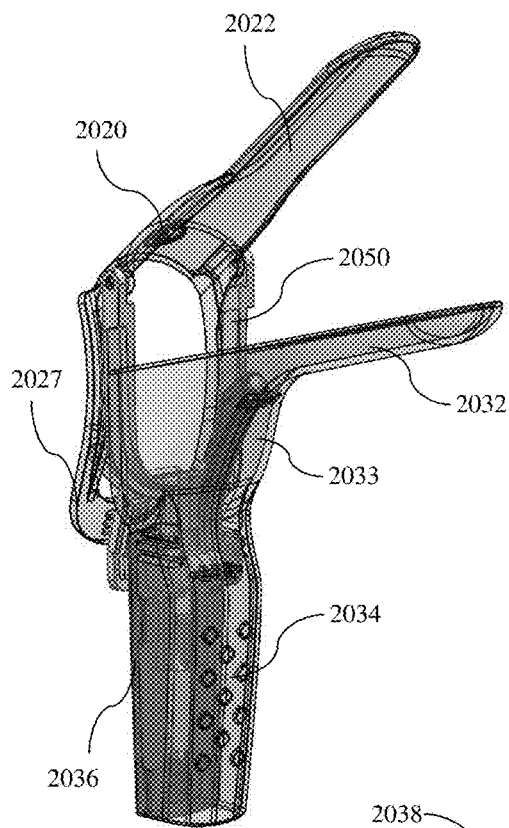
FIGS. 10A-10B show a speculum with a ninth embodiment of an illumination assembly of the present invention that allows for battery removal.
Figure 10B:
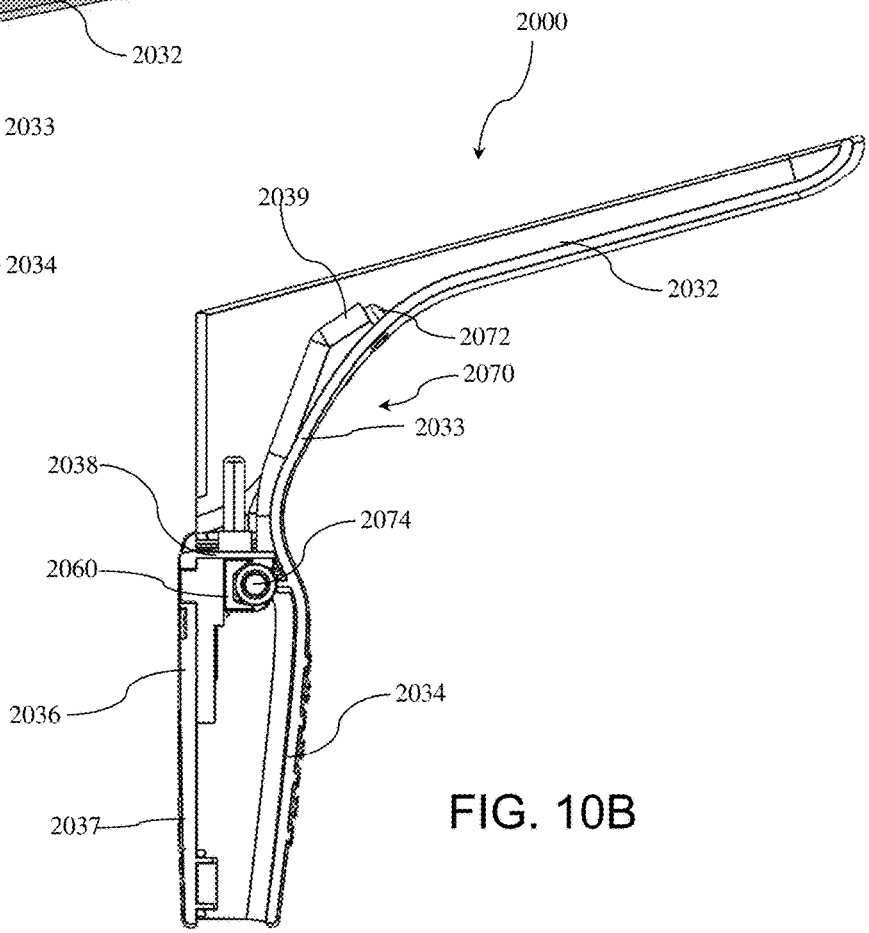

FIGS. 10A-10B show a general assembled configuration of the speculum 2000 of this embodiment. The speculum 2000 includes an upper member 2020 comprising an upper blade 2022 and an operating mechanism 2027, a lower member 2030 comprising a lower blade 2032, a handle 2034 and a rear faceplate assembly 2036 that engages with the handle 2034, and a linear support member 2050 which hingedly engages with the upper member 2020 for angular adjustment between the upper and lower blades, and slidably engages with the rear faceplate assembly 2036 for vertical adjustment between the upper and lower blades. The speculum 2000 includes an illumination assembly 2070 comprising at least one light source 2072, such as an LED or similar light emitting device, one or more batteries 2074 and wires (not shown) electrically connecting the light source 2072 with the one or more batteries. The illumination assembly may also include an activation device (not shown), which can be in a form of a pull tab, a button, a switch, a motion detector or the like, for activating the light source 2072 from on OFF state to an ON state and vice versa.

Figures 11A, 11B:
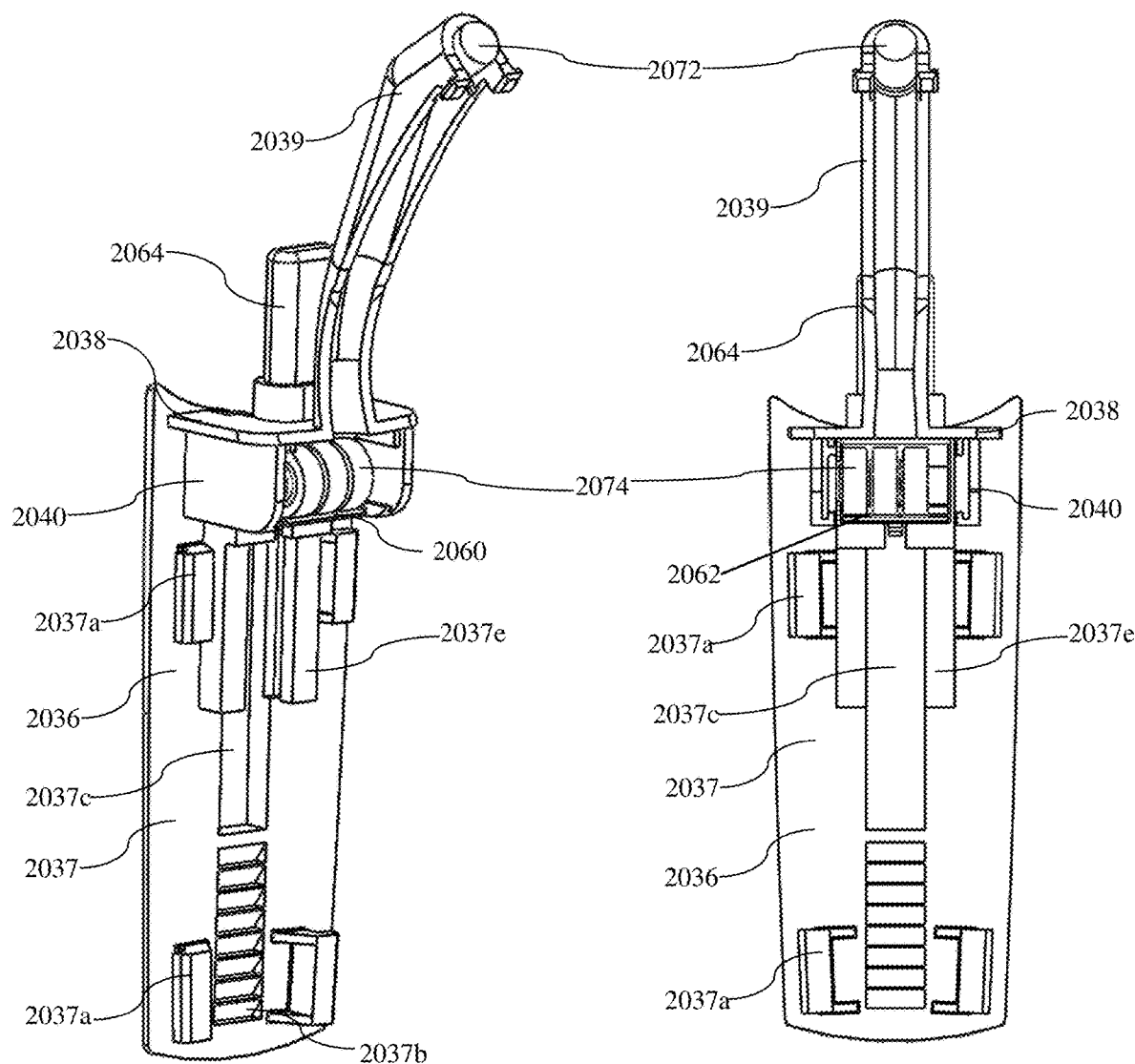
FIGS. 11A-11B show the ninth embodiment of the illumination assembly of FIGS. 10A-10B in more detail with a battery compartment in a retained state.

As shown in FIG. 10B and shown in more detail in FIGS. 11A and 11B, the rear face plate assembly 2036 includes a rear faceplate 2037 that engages with sidewalls of the handle 2034 and forms a rear wall of the handle 2034. The rear faceplate assembly 2036 also includes a shelf portion 2038 which extends from an upper end of the rear faceplate 2037 and an illumination assembly cover 2039 which extends from the shelf portion 2038. The illumination assembly cover 2039 extends along an inner surface of a front wall of the handle 2034 and along a curved portion 2033 that connects the handle and the lower blade 2032. The illumination assembly cover 2039 is open on the side that abuts the inner surface of the handle 2034 and the curved portion 2033, and encloses the wires connecting the batteries 2074 and the light source 2072. In this illustrative embodiment, the illumination assembly cover 2039 also partially encloses the light source 2072, which protrudes from an end of the illumination assembly cover 2039. In the present illustrative embodiment, the illumination assembly cover 2039 is engaged with the curved portion 2033 using tabs formed on the illumination assembly cover that engage with corresponding slots formed in the curved portion 2033. However, in other embodiments, the illumination assembly cover 2039 may engage with the handle 2034 and/or with the lower blade 2032.

In the embodiment shown in FIGS. 10A-10B, the illumination assembly 2070 is configured so that the light source 2072 is positioned adjacent the curved portion 2033 of the lower member. However, in other embodiments, the light source 2072 may be positioned closer to the lower blade 2032 or adjacent the lower blade 2032, at any location along the length of the lower blade 2032. In some embodiments, the illumination assembly cover 2039 may extend further than in the embodiments shown in FIGS. 10A-10B. For example, the illumination assembly cover 2039 may extend along a portion of the lower blade 2032. In some embodiments, the illumination assembly cover 2039 may also function as a smoke evacuation channel and may extend along the lower blade 2032 toward the distal end of the blade 2032.

FIGS. 11A-11D and 12A-12C show the rear faceplate assembly 2036 together with the battery compartment 2060 and the illumination assembly 2070. In FIGS. 11A-11D, the battery compartment 2060 is in the retained or operating state, while in FIGS. 12A-12C, the battery compartment is in the ejected state. In addition, FIG. 13 shows the rear face plate assembly 2036 without the battery compartment.

As shown in FIGS. 11A-11B, 12A and 13, the rear faceplate 2037 includes a plurality of engagement portions 2037a protruding from an inner surface thereof and configured to engage with corresponding protrusions formed on the inner side of the handle sidewalls. In certain embodiments, the protruding engagement portions 2037a may engage with a channel or one or more recesses formed in each of the handle sidewalls. In the illustrative embodiment of FIGS. 10-14, the inner surface of the rear faceplate 2037 includes a plurality of stop tabs 2037b for engagement with a lock tooth of the linear support member. In other embodiments, however, the rear faceplate 2037 may include a plurality of stop tabs on an opposing, outer surface thereof. As also shown in FIGS. 11A-11B, the rear faceplate 2037 includes a through recess 2037c extending along its length which is used for sliding the linear adjustment member therein so as to provide for vertical adjustment In the embodiments of FIGS. 10-14, the rear faceplate also includes rail portions 2037e protruding from the inner surface thereof and extending on each side of the through opening. The rail portions 2037e guide the linear support member 2050 when it is inserted into the through recess 2037c.

The battery compartment 2060 comprises a housing 2062 for holding the batteries 2074 in the retained state, and an operating member 2064, which can be operated by a user to cause the housing 2062 to move from the retained state to the ejected state. In the present illustrative embodiment, the operating member 2064 is a button protruding from the top surface of the housing. When the battery compartment 2060 is assembled with the rear faceplate assembly 2036, the operating member 2064 passes through an opening formed in the shelf 2038 of the rear faceplate assembly 2036. The shelf has a pair of sidewalls 2040 extending from a lower surface of the shelf and surrounding the batteries 2074 held by the battery compartment 2060 in the retained state. The sidewalls 2040, together with the housing 2062 of the battery compartment 2060 hold the batteries 2074 in place and prevent dislodgement of the batteries. One or both of the sidewalls 2040 may include coupling elements attached thereto for electrically coupling the batteries 2074 to the wires. In addition, one or more biasing members, e.g., a spring, may be used to hold the batteries 2074 in place between the sidewalls 2040.

Figure 11C:
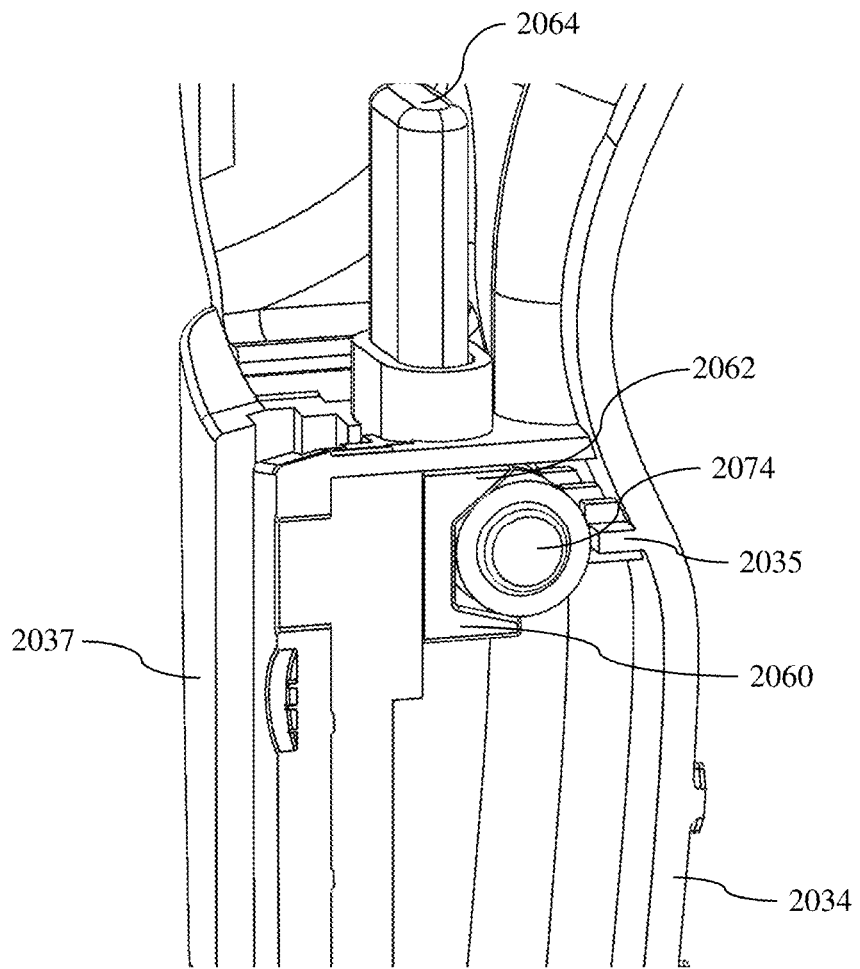
FIGS. 11C and 11D show cross-sectional view of the illumination assembly of FIGS. 11A-11B.
Figure 11D:
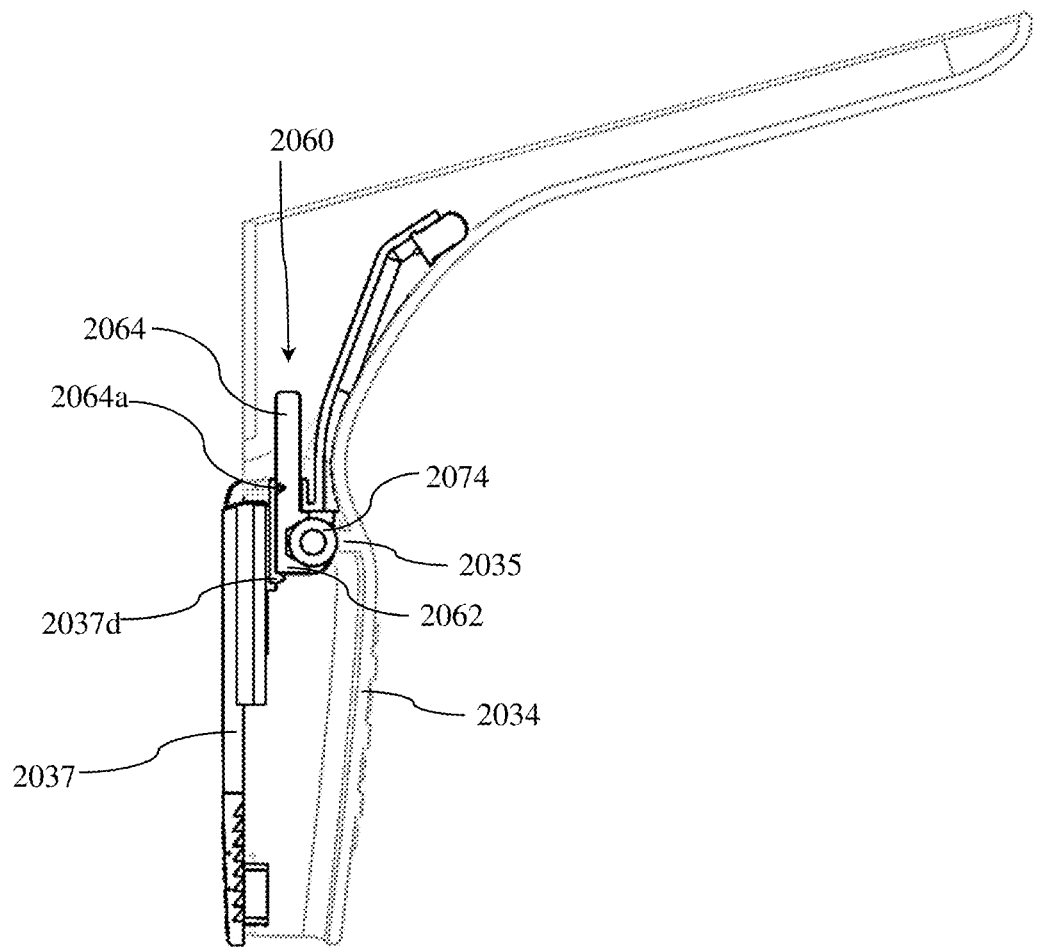

FIGS. 11C-11D show a cross-section of the speculum in which battery compartment 2060 is engaged with the rear face plate assembly 2036 in the retained state. As shown in the close-up view of FIG. 11C, the housing 2062 is a C-shaped housing which has an open side and holds the batteries 2074 against a projection 2035 formed on an inner front surface of the handle. Thus, in the retained state, the batteries 2074 are held in the C-shaped housing 2062 and are supported from the opposite side by the projection 2035 formed on the inner surface of the handle. Moreover, as described above, the batteries 2074 are also retained in their position by the sidewalls 2040 shown in FIGS. 11A-11B. The projection 2035 may be shaped as a beam with a plurality of ribs traversing the beam, as shown in FIGS. 11C and 12B. However, the shape of the projection 2035 may vary depending on the type of batteries used and the arrangement of the batteries in the housing 2062.

As shown in FIG. 11D, in the retained state, the battery compartment 2060 is locked in place relative to the rear face plate 2037 by a locking mechanism. In the illustrative embodiment shown in FIG. 11D, the locking mechanism is a snap arm 2037d formed at a top portion of the rear faceplate 2037 which includes an arm having some flexibility/elasticity and a lock tooth which engages with the bottom surface of the battery compartment 2060. In this way, the top surface of the housing 2062 of the battery compartment prevents the battery compartment from moving in an upward direction relative to the rear faceplate 2037 and the snap arm 2037d prevent the battery compartment 2060 from moving in a downward direction relative to the rear faceplate 2037. Alternatively, a notch may be provided in the bottom portion of the battery compartment 2060 for engagement with the snap arm 2037d so as to prevent movement of the battery compartment. FIG. 13 shows a more detailed view of the snap arm 2037d, which is formed in the rear faceplate 2037 and extends into the through recess 2037c in the rear faceplate 2037. In some embodiments, instead of the snap arm or in addition to the snap arm, other mechanical engagements may be used to retain the battery compartment in the retained state and in the ejected state. For example, the button 2064 may include a lip formed at or near its top surface, with the periphery of the lip being greater than the opening in the shelf 2038. The lip would prevent the button 2064 from being pushed through the opening in the shelf 2038 past the lip and from falling out together with the batteries. Other types of retaining means may be used for preventing the battery compartment from falling out when the button is moved to the ejected state.

As also shown in FIG. 11D, the operating member 2064 includes a notch 2064a or a recess in its surface that faces the rear faceplate 2037 when assembled. This notch 2064a engages the snap arm 2037d in the ejected state to prevent removal of the battery compartment 2060 from the speculum. When sufficient force is applied to the operating member 2064 in the retained state, the snap arm 2037d disengages from the bottom of the housing 2062 and the battery compartment 2060 is moved from the retaining state to the ejected state shown in FIGS. 12A-12C.

Figure 12A:
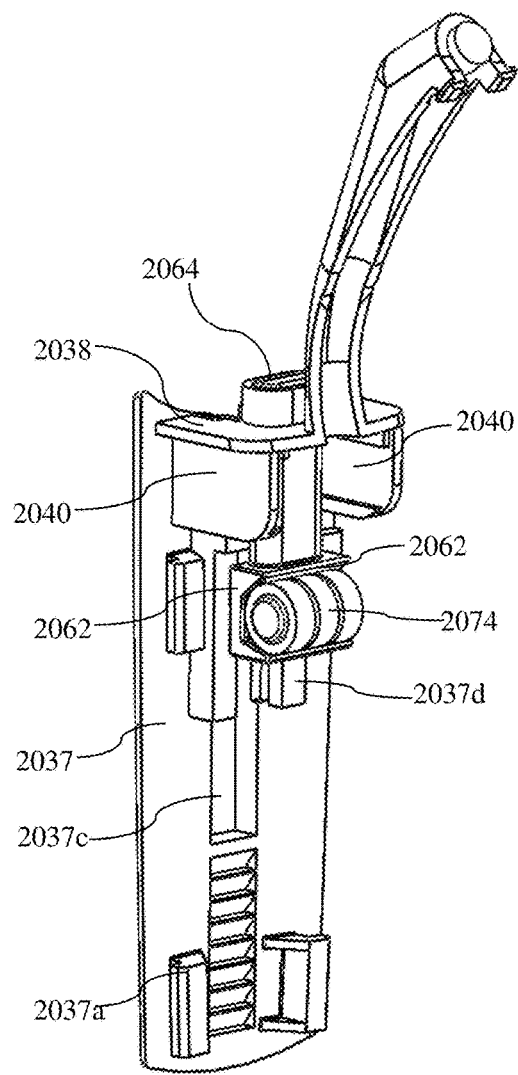
FIGS. 12A-12C show the illumination assembly of FIGS. 11A-11D with the battery compartment in an ejected state.
Figure 12B:
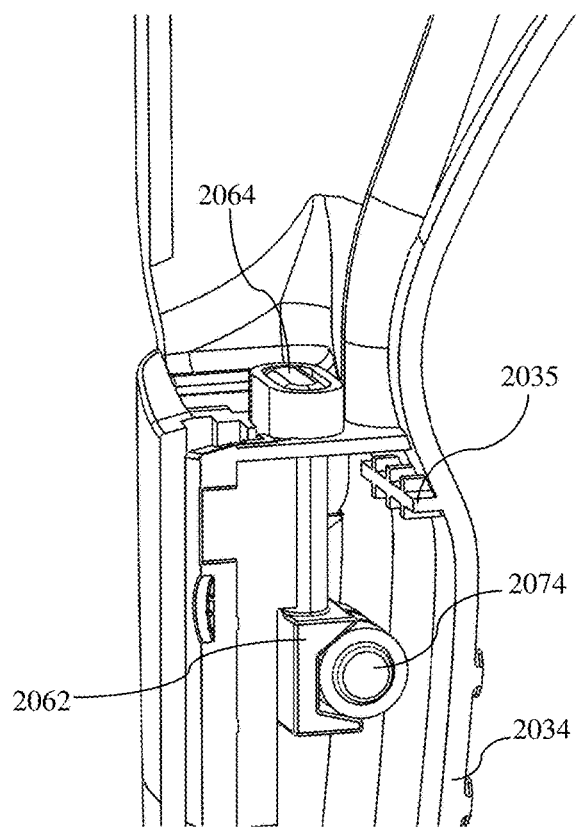
Figure 12C:
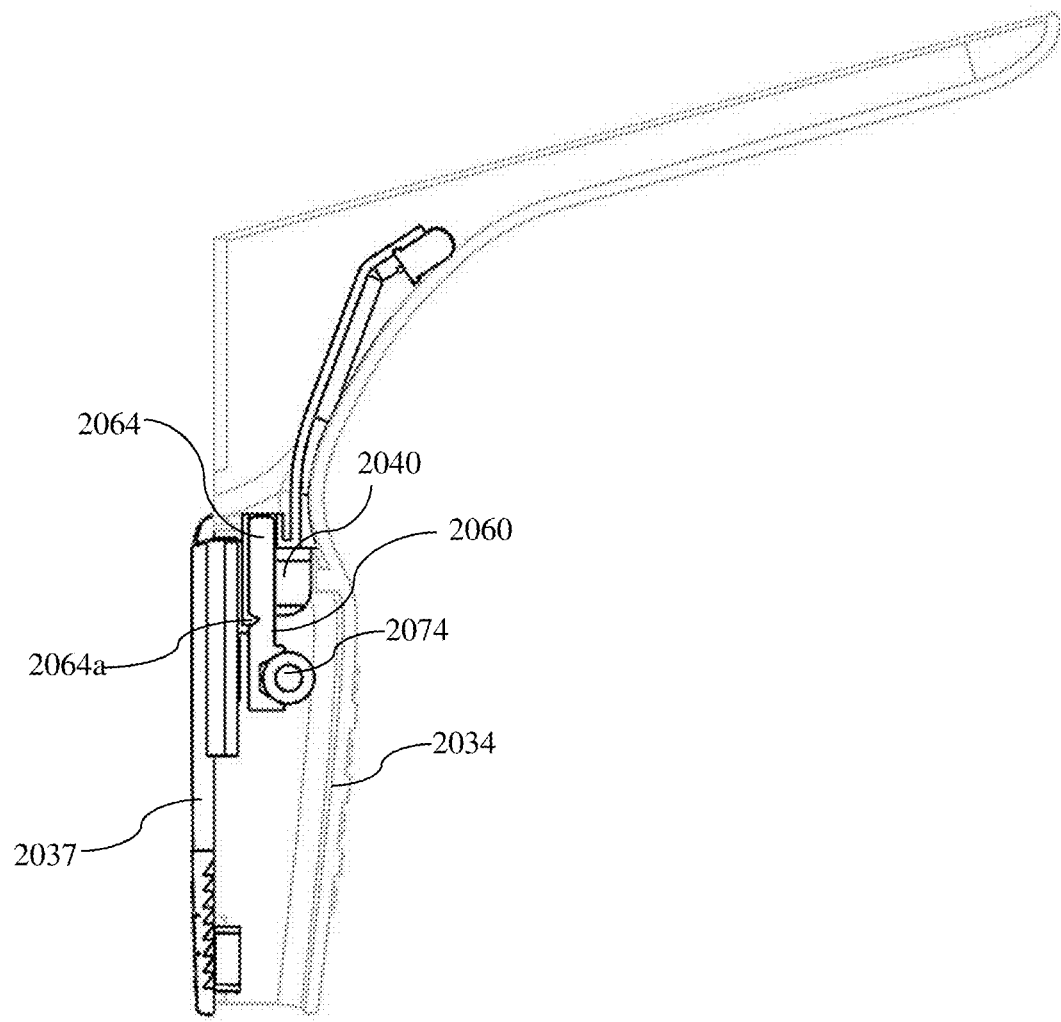
Figure 13:
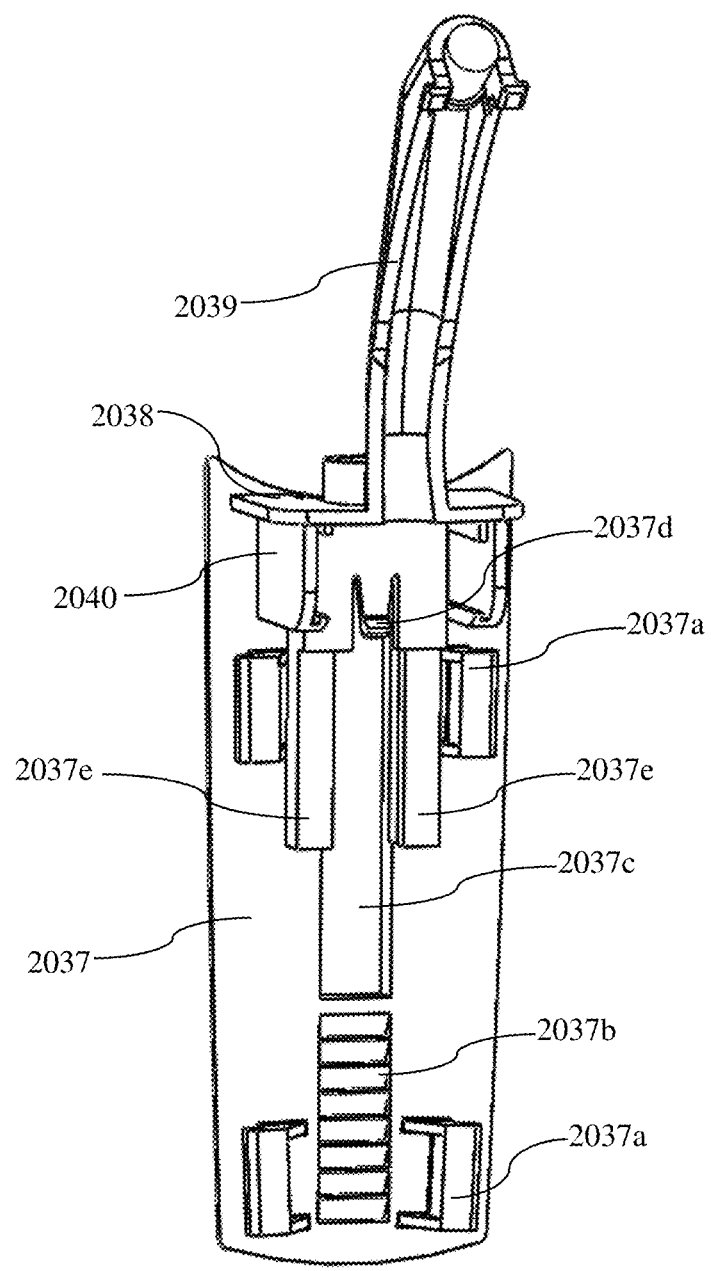
FIG. 13 shows a rear faceplate portion of the illumination assembly of FIGS. 11A-11D without the battery compartment.

FIG. 12A shows the rear face plate assembly 2036 together with the battery compartment 2060 in the ejected state, and FIGS. 12B-12C show a cross-sectional view of the speculum 2000 with the battery compartment 2060 in the ejected state. As can be seen in FIGS. 12A-12C, in the ejected state, the batteries 2074 are no longer pressed against the projection 2035 on the inner surface of the handle and are removed from the space between the sidewalls 2040 that extend from the shelf 2038. Since the batteries are no longer retained on all sides by the housing 2062, the sidewalls 2040 and the projection 2035, they can be easily dislodged from the housing 2062 and removed from the open bottom end of the handle 2034. In the present illustrative embodiment, the handle 2034 is shaped so that the handle is smaller in circumference in the area of the projection 2035 and larger in circumference in the area below the projection 2035. As shown in FIGS. 12B and 12C, the front wall of the handle protrudes outwardly below the projection 2035. This configuration provides additional space for releasing the batteries from the housing 2062 and for allowing the batteries to easily fall through the handle to be removed from the bottom opening in the handle.

Moreover, as can be seen in FIG. 12C, the battery compartment 2060 is locked in place in the ejected state by the snap arm 2037d, which is engaged with the notch 2064a in the operating member 2064. This prevents removal of the battery compartment 2060 together with the batteries, which could contaminate the batteries with biological materials and would require subsequent separation of the battery compartment from the batteries to be recycled.

Although the batteries in the embodiment of FIGS. 10-12 are removed though the open bottom end of the handle, other variations are also contemplated. For example, the batteries may be removed from a cutout formed in one of the sidewalls of the handle 2034 or from a cutout formed in the rear faceplate 2037. In addition, the operating member 2064 in the embodiments of FIGS. 10-12 is configured as a push-button. In other embodiments, a pulling mechanism may instead be used to pull the battery compartment 2060 downward so as to release the batteries from the battery compartment.

Moreover, although FIGS. 10-12 show the battery removal mechanism being used in a speculum, it is understood that this mechanism may be adapted for use in other devices, such as retractors, laryngoscopes, anoscopes, suction devices, and other medical devices. For example, the battery removal mechanism may be adapted for use in a surgical retractor by omitting the upper member 2020 and the linear support member 2050 and using a substantially the same mechanism for battery removal in a retractor that includes a handle 2034, a retractor blade extending at an angle with respect to the handle and the rear faceplate assembly 2036 as described above (similar to FIG. 10B). In another example, the battery removal mechanism may be adapted for use in an anoscope by omitting the upper member 2020 and the linear support member 2050 and by modifying the shape of the lower blade.

Figure 14A:
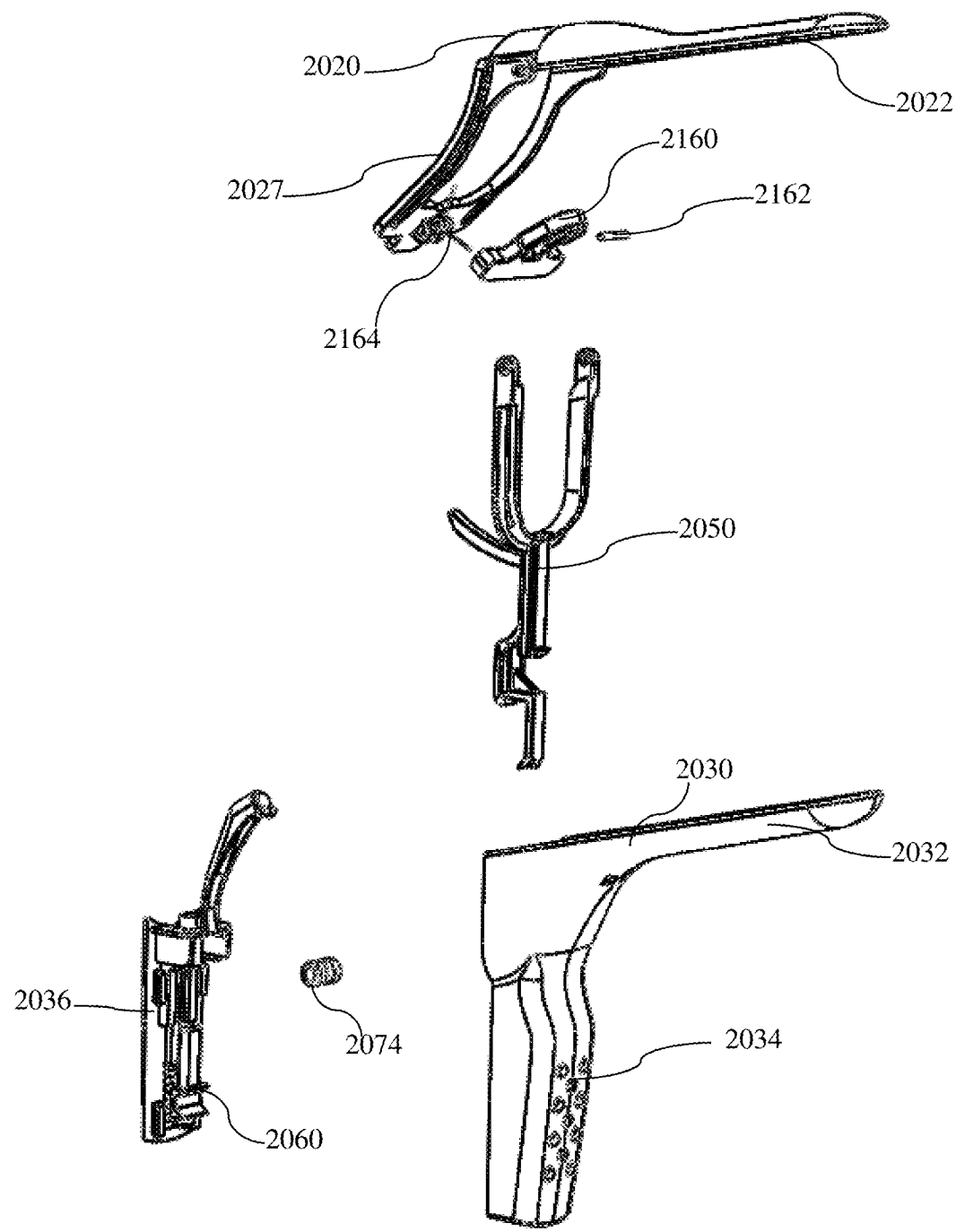
FIG. 14A shows an exploded view of the speculum of FIGS. 10A-13.

The illustrative embodiment of the speculum in FIGS. 10-13 is assembled as shown in FIGS. 14A-14G. FIG. 14A shows an exploded view of the speculum, which includes the lower member 2030 with the handle 2034 and the lower blade 2032, the upper member 2020 with the upper blade 2022 and an operating member 2027, the linear support member 2050, the rear faceplate assembly 2036 together with the battery compartment 2060, batteries 2074, a rocker 2160 for angular adjustment, a biasing member 2164 and a pivot pin 2162 for attaching the rocker 2160. FIGS. 14B-14G show an illustrative sequence of assembling the speculum of FIGS. 10-13.

Figure 14B:
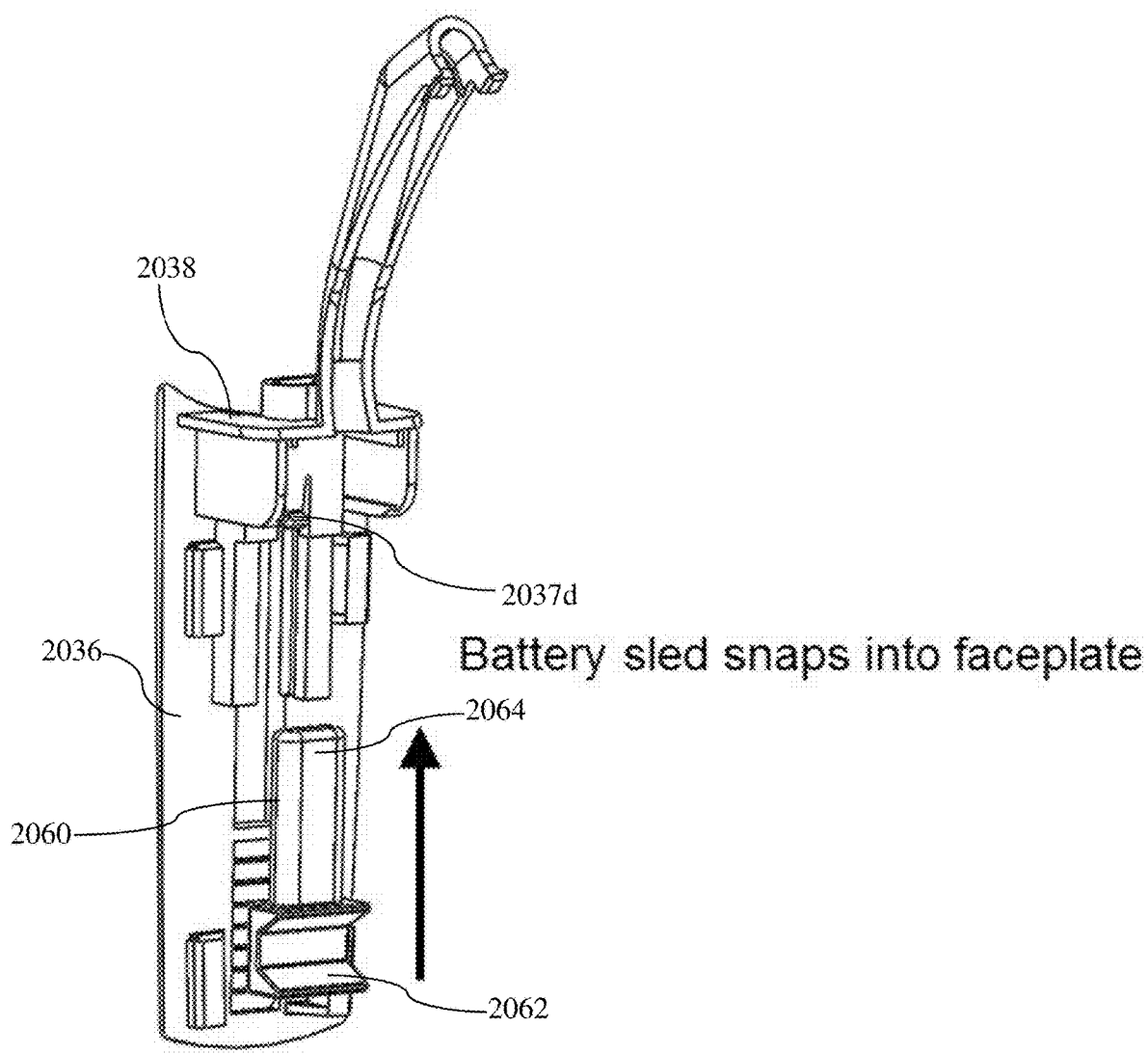
FIGS. 14B-14G show an illustrative sequence of assembling the speculum of FIGS. 10A-13.
Figure 14C:
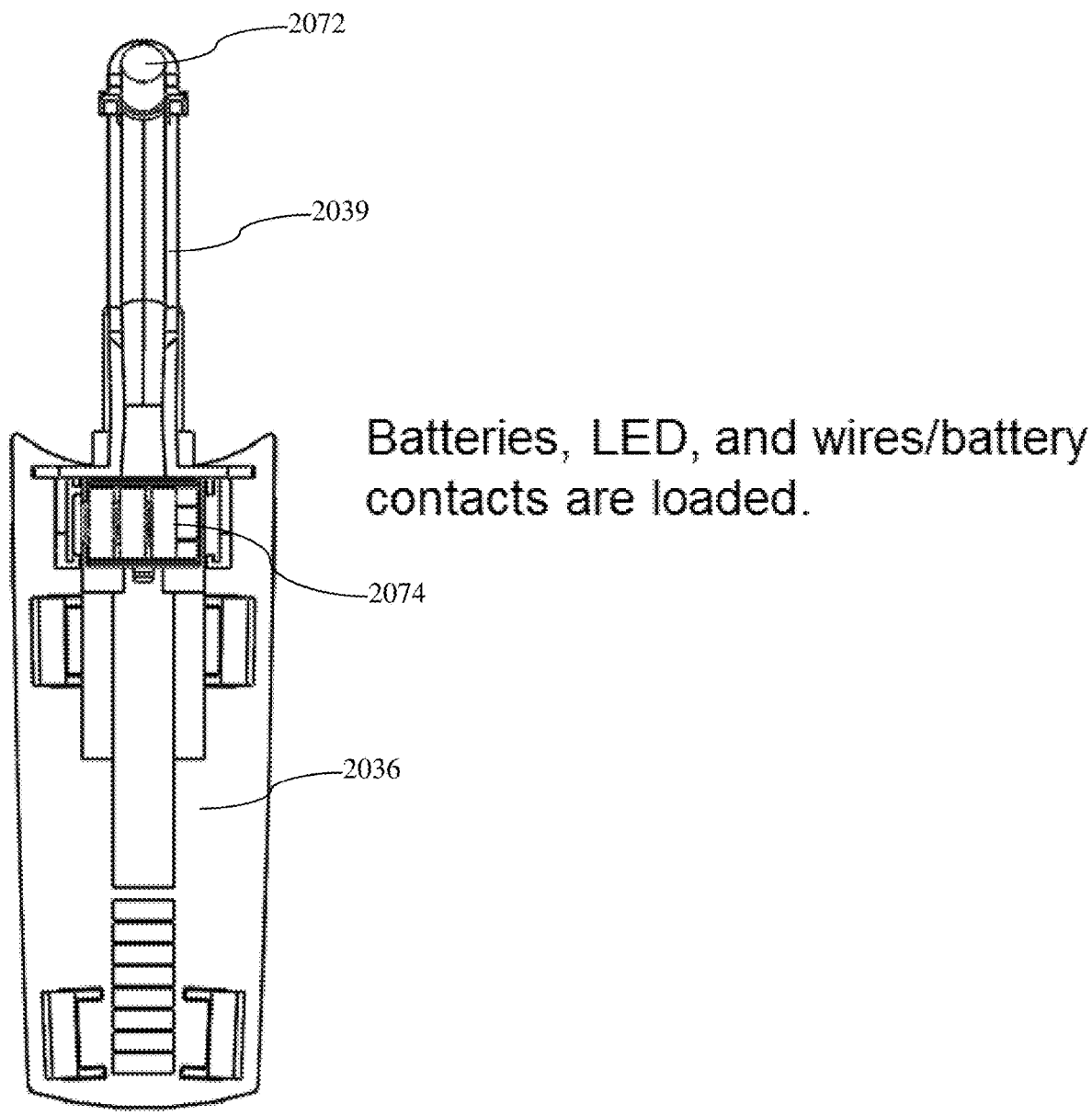

As shown in FIG. 14B, the battery compartment 2060 is assembled with the rear faceplate assembly 2036 by inserting the button 2064 into the opening in the shelf 2038 of the rear faceplate assembly 2036. When the button 2064 is fully inserted into the opening in the shelf 2038, the snap arm 2037d engages with the bottom surface of the housing 2062. After the battery compartment 2060 is snapped in to engage with the rear faceplate assembly 2036, the batteries 2074 are inserted into the housing 2062, as shown in FIG. 14C, and are held by the housing and between the sidewalls 2040 extending from the shelf 2038. At the time of, or prior to, positioning the batteries, battery contacts are loaded to allow for connection of the batteries to wires. In addition, as shown in FIG. 14C, the light source 2072 is positioned to be held by the end of the illumination assembly cover 2039 and the wires are loaded to connect the light source 2072 to the battery contacts and to be enclosed by the illumination assembly cover 2039. As shown in FIG. 14C, the illumination assembly 2070 is assembled together with the rear faceplate assembly 2036 and the battery compartment 2060.

Figure 14D:
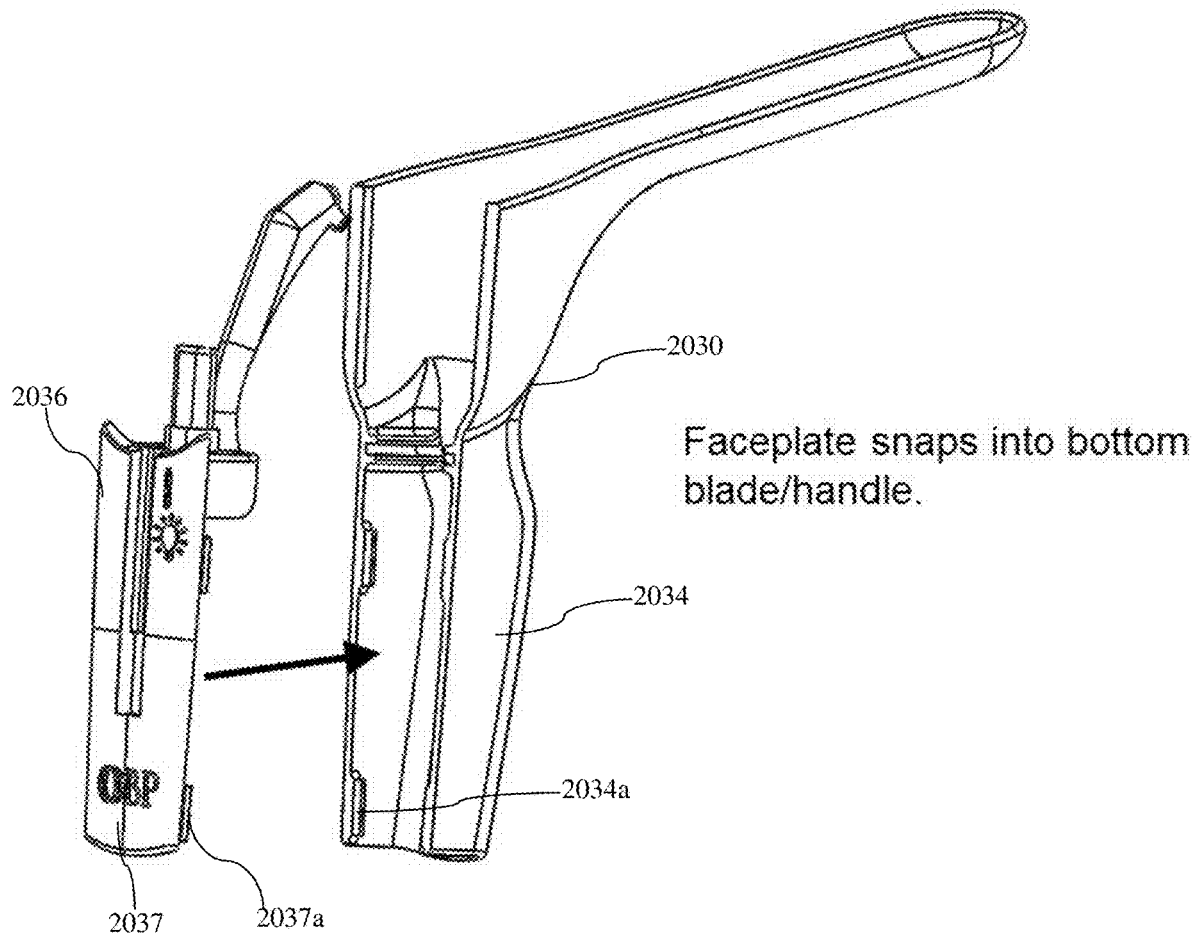

As shown in FIG. 14D, the resulting assembly of FIG. 14C is then assembled together with the lower member 2020. In the illustrative embodiment of FIG. 14D, the rear faceplate assembly 2036 snaps into the rear of the handle 2034 of the lower member 2020 to form the rear wall of the handle 2034. As described above, the engagement protrusions 2037a on the inner surface of the rear faceplate 2037 snap to engage with corresponding protrusions 2034a formed on the inner surface of the handle sidewalls. In other embodiments, other types of engagement may be used for assembling the rear faceplate assembly 2036 with the lower member 2020. For example, the sidewalls of the handle may include channels formed on the inner surfaces thereof for engagement with the engagement protrusions 2037a on the rear faceplate 2037 by sliding the engagement protrusions 2037a into the channels. In other embodiments, the sidewalls of the handle may include recesses for engaging with the engagement protrusions 2037a. In yet other embodiments, the sidewalls of the handle may include protrusions that engage with corresponding recesses formed in the rear faceplate 2037. Other types of engagements may be used for coupling the faceplate assembly 2036 with the lower member 2020.

Figure 14E:
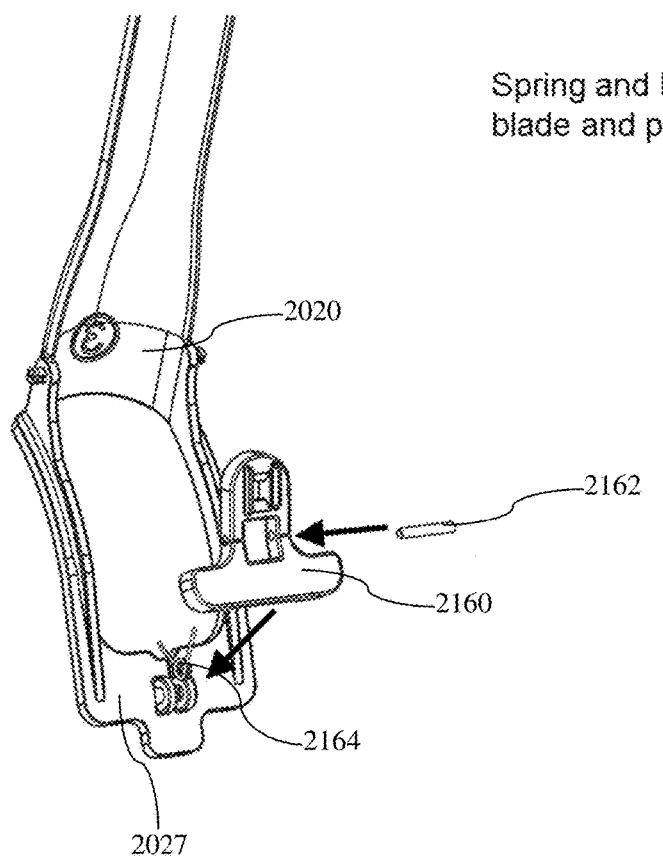

As shown in FIG. 14E, the rocker 2160, the biasing member 2164 and the pin 2162 of the angular adjustment mechanism is assembled with the operating member 2027.

Figure 14F:
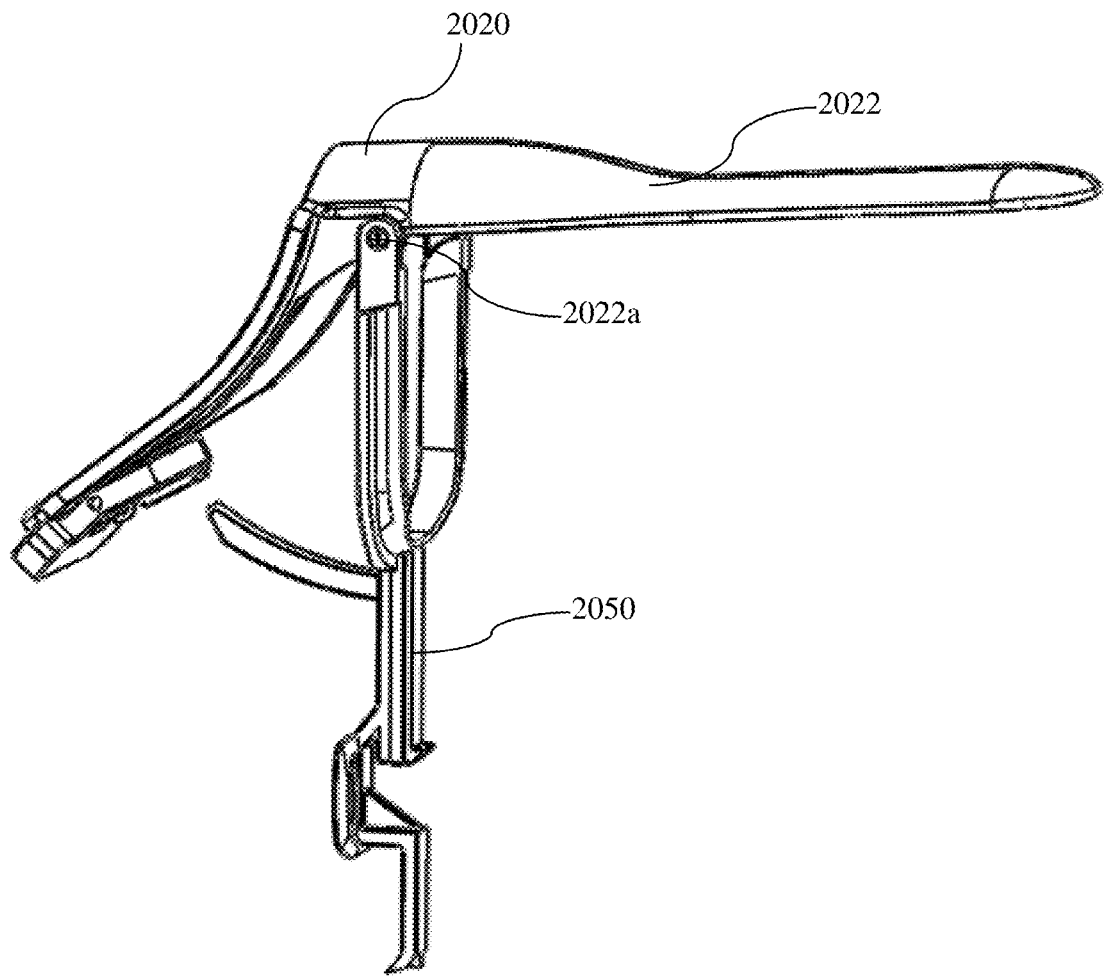
Figure 14G:
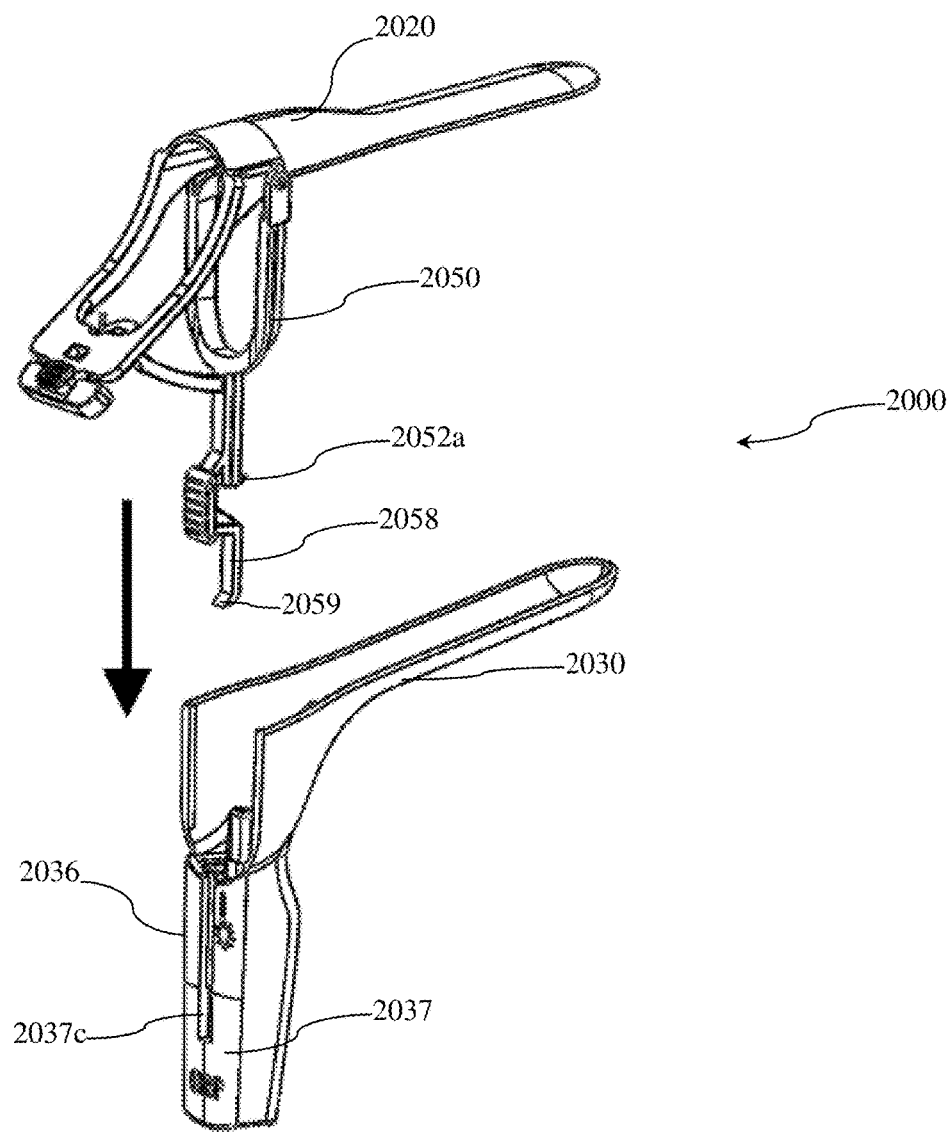

As shown in FIG. 14F, the top member 2020 is assembled together with the linear support member 2050. In the embodiment of FIG. 14F, hinge protrusions 2022a are formed on the outer sides of a proximal end of the upper blade 2022. The linear support member 2050 includes a yoke portion (U-shaped portion) extending from its elongated body with each leg of the yoke portion including an opening for engaging with the corresponding hinge protrusion 2022a. To assemble the upper member 2020 with the linear support member, the hinge protrusions 2022a are snapped into corresponding openings in the yoke portion for a hinge coupling therebetween. In other embodiments, the legs of the yoke portion may include inwardly facing protrusions and the proximal end of the blade 2022 may include corresponding openings for insertion of the protrusions on the yoke portion. Other types of couplings may be used to form a hinge coupling between the upper member 2020 and the linear support member 2050. As shown in FIG. 14G, the top assembly formed in FIG. 14F is then assembled together with the bottom assembly formed in FIG. 14D by inserting the linear support member 2050 into the through recess 2037c formed in the rear faceplate 2037. When the linear support member 2050 is inserted into the through recess 2037c, the engagement arm 2058 of the linear support member 2050 is inserted into the through recess 2037c and slid below the through recess 2037c so that the locking tooth 2059 on the engagement arm 2058 engages with stop tabs formed on the inner surface of the rear faceplate 2037. Also, when the linear support member 2050 is inserted into the through recess 2037c beyond the predetermined position, the retaining projection 2052a on the elongated body 2052 of the linear support member 2050 engages with the rear faceplate assembly 2036 to prevent removal and disengagement of the linear support member 2050 from the rear faceplate assembly 2036. The resulting disposable speculum 2000 has mechanical engagements between the different elements, which makes the speculum easy to assemble and which are sufficiently strong to withstand in-use conditions. The order in which the elements of the speculum 2000 are assembled are not limited to the order shown in FIGS. 14B-14G, and may be varied.

The materials used for forming the speculum of FIGS. 10-14 are similar to those of other speculums shown in other figures and described above. In certain embodiments, the speculum components are formed from plastic materials. Exemplary plastic materials that may be used for constructing the speculum of the present invention include, but are not limited to, polypropylene, polystyrene, and any composite of more than one of these plastics and polymers. The upper and lower members and the rear faceplate assembly may be molded from a colorless transparent or translucent plastic material, such as acrylic plastic, polycarbonate or the like. The rocker may be made from the same or similar materials as the speculum or from metallic materials. The linear support member may be formed from a polyester or polyamide material, such as nylon, or the like. The biasing member (spring) and the pin may be formed from metallic materials or from polymers and plastics. All of these components may be formed by injection molding, extrusion, using a 3D printer or any other suitable technique. In certain embodiments, the materials for forming the speculum, including the upper and lower members, the rear faceplate assembly, the rocker and/or the linear support member, of the present invention include glass-fiber reinforced polymers, polyacrylamide compounds, thermoplastic crystalline polymers, thermoplastic crystalline polymers of aromatic diamines and aromatic dicarboxylic anhydrides, glass-fiber reinforced polyacrylamides, and other materials having sufficient rigidity and strength. Although in the illustrative embodiments, plastic and/or polymer materials are used for the components of the speculum, in other embodiments, some or all of the components may be formed from metallic or fiberglass materials.

Although the embodiments described above are shown with a speculum, it is understood that the battery removal mechanisms may be used with other medical devices that use batteries, either as part of the illumination assembly or as part of another assembly that requires batteries. In addition to the specific embodiments described above, other variations may be made for safe removal of batteries without contaminating them with biological materials, as would be appreciated to those of ordinary skill in the art. Therefore, it is to be understood that other expedients/variations may be employed but that stay within the meaning, scope and spirit of the invention.

In all cases it is understood that the above-described arrangements are merely illustrative of the many possible specific embodiments which represent applications of the present invention. Numerous and varied other arrangements, including use of different materials and various configurations of components of the speculum or another medical device, can be readily devised without departing from the spirit and scope of the invention.

This application claims priority to provisional patent application Nos. 62/649,190 filed on Mar. 28, 2018, 62/574,969 filed on Oct. 20, 2017 and 62/574,412 filed on Oct. 19, 2017, the disclosures of which are incorporated herein by reference.

We claim:

1. A battery-powered medical device comprising:
an outer housing having an opening formed therein;
at least one power source housed within the outer housing, the outer housing being configured to at least partially enclose the at least one power source so as to prevent contamination of the at least one power source with biohazardous materials, and the at least one power source being removable from the outer housing via the opening;
a cover configured to cover the opening in the outer housing and to retain the at least one power source within the outer housing, and
an actuator provided within the outer housing that directly engages with a portion of the at least one power source when the cover covers the opening in the outer housing,
wherein the cover is configured to be operated to expose the opening in the outer housing,
wherein when the cover is operated to expose the opening, the actuator is configured to undergo a rotational motion with respect to the outer housing to pull the at least one power source from the outer housing and the outer housing is configured to release the at least one power source via the opening without requiring physical contact between the user and the at least one power source,
wherein the outer housing comprises a handle and an operative portion coupled to the handle, and
wherein the opening in the outer housing extends through at least a portion of the handle in a direction that is substantially perpendicular to a longitudinal axis of the handle.

2. The battery-powered medical device of claim 1, wherein the actuator loops around a portion of the at least one power source.

3. The battery-powered medical device of claim 1, wherein the medical device is one of a retractor and a suction device.

4. The battery-powered medical device of claim 1, wherein the at least one power source is housed in the handle.

5. The battery-powered medical device in accordance with claim 1, further comprising an illumination assembly including at least one light source, wherein the at least one power source is configured to power the at least one light source.

6. The battery-powered medical device in accordance with claim 5, wherein the at least one light source is provided on the operative portion and the at least one power source is housed in the handle.

7. The battery-powered medical device of claim 1, wherein the outer housing has an end region and a sidewall extending from the end region, and wherein the opening is formed in the sidewall such that the at least one power source is removable from the outer housing through the opening in the sidewall along a lateral direction that is perpendicular to the longitudinal axis of the handle.

8. The battery-powered medical device in accordance with claim 1, wherein the actuator extends across the opening in the outer housing.

* * * * *